United States Patent
Juillerat et al.

(10) Patent No.: US 10,815,500 B2
(45) Date of Patent: Oct. 27, 2020

(54) TRANSCRIPTION ACTIVATOR-LIKE EFFECTOR (TALE) FUSION PROTEIN

(71) Applicants: Alexandre Juillerat, Paris (FR); Philippe Duchateau, Draveil (FR); Cellectis, Paris (FR)

(72) Inventors: Alexandre Juillerat, Paris (FR); Philippe Duchateau, Draveil (FR)

(73) Assignee: Cellectis, Paris (FR)

( * ) Notice: Subject to any disclaimer, the term of this patent is extended or adjusted under 35 U.S.C. 154(b) by 90 days.

(21) Appl. No.: 14/405,283

(22) PCT Filed: Jun. 5, 2013

(86) PCT No.: PCT/IB2013/001741
§ 371 (c)(1),
(2) Date: Dec. 3, 2014

(87) PCT Pub. No.: WO2013/182910
PCT Pub. Date: Dec. 12, 2013

(65) Prior Publication Data
US 2015/0203871 A1 Jul. 23, 2015

Related U.S. Application Data

(60) Provisional application No. 61/655,747, filed on Jun. 5, 2012.

(51) Int. Cl.
*C12N 15/90* (2006.01)
*C12N 9/22* (2006.01)
*C12N 15/10* (2006.01)

(52) U.S. Cl.
CPC .......... *C12N 15/907* (2013.01); *C12N 9/22* (2013.01); *C12N 15/10* (2013.01); *C07K 2319/80* (2013.01)

(58) Field of Classification Search
CPC ............................ C12N 9/22; C07K 2319/80
See application file for complete search history.

(56) References Cited

U.S. PATENT DOCUMENTS

| | | | | |
|---|---|---|---|---|
| 8,586,526 B2* | 11/2013 | Gregory | ................ | C12N 15/62 435/23 |
| 2007/0218528 A1* | 9/2007 | Miller | ................ | C07K 14/4702 435/91.2 |
| 2011/0145940 A1 | 6/2011 | Voytas | | |
| 2011/0201118 A1* | 8/2011 | Yang | ................ | C12N 15/8213 435/441 |
| 2011/0207221 A1* | 8/2011 | Cost | ......... | C12N 9/22 435/440 |
| 2014/0115726 A1* | 4/2014 | Duchateau | ............. | C12N 9/22 800/13 |

FOREIGN PATENT DOCUMENTS

WO 2012/058458 A2 5/2012
WO 2012/138927 A2 10/2012

OTHER PUBLICATIONS

Li et al. Modularly assembled designer TAL effector nucleases for targeted gene knockout and gene replacement in eukaryotes. Nucleic Acids Research, vol. 39, No. 14, pp. 6315-6325, Mar. 31, 2011.*
Ting Li et al: "TAL nucleases (TALNs): hybrid proteins composed of TAL effectors and FokI DNA-cleavage domain", Nucleic Acids Research, Oxford University Press, GB, vol. 39, No. 1, Jan. 1, 2011 (Jan. 1, 2011), pages 359-372.
Claudio Mussolino et al: "TALE nucleases: tailored genome engineering made easy", Current Opinion in Biotechnology, vol. 23, No. 5, Feb. 17, 2012 (Feb. 17, 2012), pp. 644-650.
Jeffrey C Miller et al: "A TALE nuclease architecture for efficient genome editing", Nature Biotechnology, Nature Publishing Group, United States, vol. 29, No. 2, Feb. 1, 2011 (Feb. 1, 2011), pp. 143-148.
Christian et al. (2010) "Targeting DNA double-strand breaks with TAL effector nucleases." Genetics 186(2): 757-61.
Deng et al. (2012) "Structural basis for sequence-specific recognition of DNA by TAL effectors." Science 335(6069): 720-3.
Mak et al. (2012) "The crystal structure of TAL effector PthXo1 bound to its DNA target." Science 335(6069): 716-9.
Li et al., Modularly assembled designer TAL effector nucleases for targeted gene knockout and gene replacement in eukaryotes, Nucleic Acids Research, 2011, vol. 39, No. 14 6315-6325.
Li et al., TAL nucleases (TALNs): hybrid proteins composed of TAL effectors and FokI DNA-cleavage domain, Nucleic Acids Research, 2011, vol. 39, No. 1 359-372.

* cited by examiner

*Primary Examiner* — Jennifer Dunston
(74) *Attorney, Agent, or Firm* — Arrigo, Lee, Guttman & Mouta-Bellum LLP

(57) ABSTRACT

The present invention relates to Transcription Activator-Like Effector (TALE) derived proteins that allow efficient targeting and/or processing of double stranded nucleic acid sequences. The proteins of the invention are typically chimeric protein monomers composed of a core scaffold comprising Repeat Variable Dipeptide regions (RVDs) having binding specificity to a DNA target sequence, to which is fused a catalytic domain to its N-terminus. This later catalytic domain, which can be a monomer of a nuclease, is placed at this position to possibly interact with another catalytic domain fused to another TAL monomer, such that, when the monomers are binding to their respective target DNA sequences, both catalytic domains form a catalytic entity likely to process DNA in the proximity of these target sequences. This new TAL architecture makes it possible to target only one DNA strand, which is not the case, for instance, with classical TALEN architectures. The present invention also relates to vectors encoding such proteins and compositions or kits in which Transcription Activator-Like Effector (TALE) proteins of the present invention are used.

Figure 1:
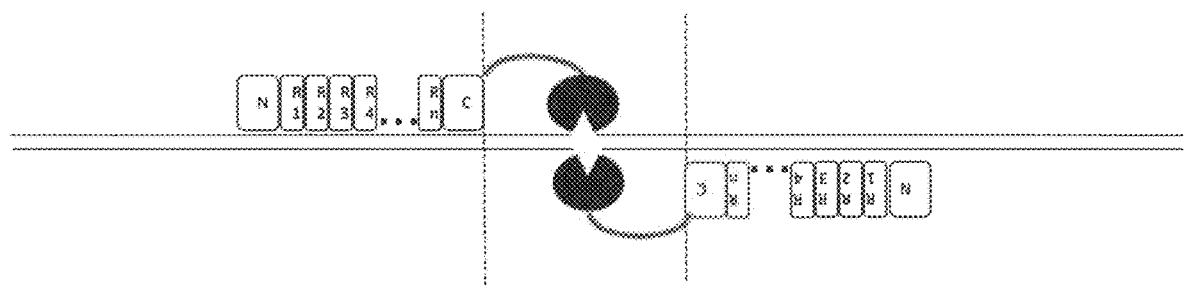

12 Claims, 5 Drawing Sheets
Specification includes a Sequence Listing.

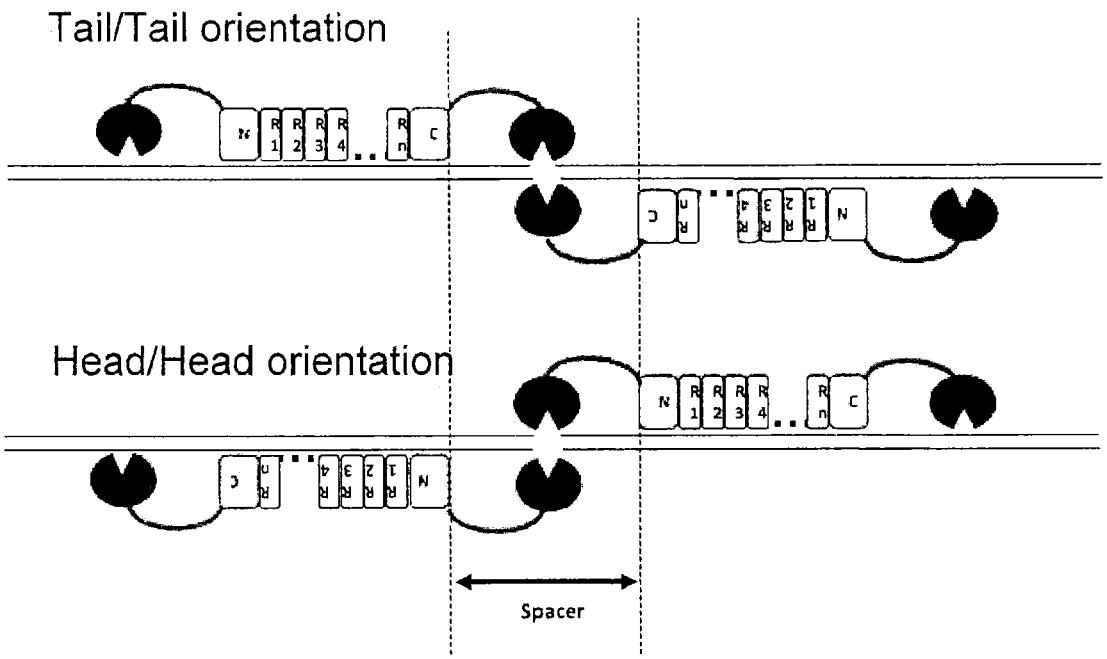

Legend

 TALE protein N-terminal region (including truncations thereof)

 - TALE protein C-terminal region (including truncations thereof)

 TALE protein repeat region (n = final repeat; depends on construct)

... - Additional TALE repeat regions (for brevity, not shown)

 Catalytic domain for DNA strand cleavage (can be cleavase or nickase domain)

 - Protein linker region

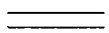 Double-strand DNA

Figure 2

Head/Tail orientation

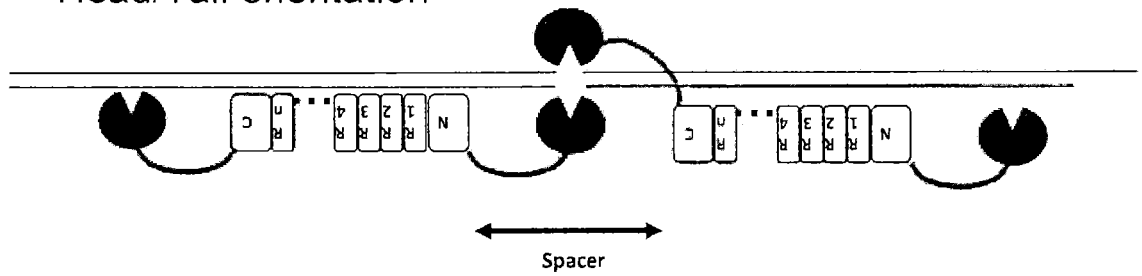

Spacer

Legend

| | | | |
|---|---|---|---|
| N | - TALE protein N-terminal region (including truncations thereof) | C | - TALE protein C-terminal region (including truncations thereof) |
| R1 | - TALE protein repeat region (n = final repeat; depends on construct) | ... | - Additional TALE repeat regions (for brevity, not shown) |
| Catalytic domain | - Catalytic domain for DNA strand cleavage (can be cleavase or nickase domain) | ⌒ | - Protein linker region |
| ——— | - Double-strand DNA | | |

Figure 3

TRANSCRIPTION ACTIVATOR-LIKE EFFECTOR (TALE) FUSION PROTEIN

The instant application contains a Sequence Listing which has been submitted electronically in ASCII format and is hereby incorporated by reference in its entirety. Said ASCII copy, created on Dec. 3, 2014, is named Sequence_Listing.txt and is 92,650 bytes in size.

FIELD OF THE INVENTION

The present invention relates to Transcription Activator-Like Effector (TALE) derived proteins that allow to efficiently target and/or process double stranded nucleic acid sequences. The proteins of the invention are typically chimeric protein monomers composed of a core scaffold comprising Repeat Variable Dipeptide regions (RVDs) having binding specificity to a DNA target sequence, to which is fused a catalytic domain to its N-terminal. This later catalytic domain, which can be a monomer of a nuclease, is placed at this position to possibly interact with another catalytic domain fused to another TAL monomer, such that, when said monomers are binding to their respective target DNA sequences, both catalytic domains form a catalytic entity likely to process DNA in the proximity of these target sequences. By contrast to classical TALEN architectures, this new TAL architecture makes it possible to target only one DNA strand. The present invention also relates to vectors encoding such proteins and compositions or kits in which Transcription Activator-Like Effector (TALE) proteins of the present invention are used.

BACKGROUND OF THE INVENTION

TAL effector DNA binding domains have been derived from of a recently discovered new class of proteins AvrBs3 originating from the plant pathogen *Xanthomonas*, which act as Transcription Activators in plant cells during the process of infection (Kay et al. 2007). These AvrBs3 proteins have been found to activate the transcription of some specific genes involved into the infection process by binding to specific promoter sequences. Their binding domains are composed of an array of motifs of 33-35 amino acids repeats. These repeats differ essentially by the residues 12 and 13 (di-residues), named RVDs (repeat variable diresidues), which constitute the TAL effector DNA binding domain of these proteins. The study of the RVDs in relation with the natural promoter DNA sequences targeted by these AvrBs3 proteins has revealed in 2009 that there was a specific correlation between the RVDs found within the TAL effector DNA binding domain and the nucleic acids present in the promoter sequences. As a result, a code has been established between amino acids and DNA sequences, so that it is now possible, by following said code, to engineer TAL effector DNA binding domains by assembly of selected RVDs to target specific DNA sequences (Boch, Scholze et al. 2009; Moscou and Bogdanove 2009).

Engineered TAL effector DNA binding domains have since been used with success, especially as a tool in genome engineering by fusion of a catalytic domain with nuclease activity to the C-terminal of AvrBs3-like proteins. Such fusions form endonucleases with sequence specificity called TALE nuclease or TALEN (WO 2011/072246). These TALEN have the ability to create double strand breaks at proximity of selected DNA target sequences. TALEN have been shown to be active to various extents in cell-based assays in yeast, mammalian cells and plants (Christian, Cermak et al. 2010; Li, Huang et al. 2010; Cermak, Doyle et al. 2011; Geissler, Scholze et al. 2011; Huang, Xiao et al. 2011; Li, Huang et al. 2011; Mahfouz, Li et al. 2011; Miller, Tan et al. 2011; Morbitzer, Elsaesser et al. 2011; Mussolino, Morbitzer et al. 2011; Sander, Cade et al. 2011; Tesson, Usal et al. 2011; Weber, Gruetzner et al. 2011; Zhang, Cong et al. 2011; Deng, Yan et al. 2012; Li, Piatek et al. 2012; Mahfouz, Li et al. 2012).

Up to now, researchers have classically used TALEN architecture based on the fusion of a FokI catalytic head (CH) to C-terminal truncated forms of the wild type protein AvrBs3. Despite truncation of the N-terminal domain has also been proven to be functional to a certain extend (more precisely at position 152), the N-terminal domain of TAL effector DNA binding domains have not been used for fusion with active proteins (N-terminal part of AvrBs3 has not been reported to display any real functionality).

Meanwhile, current C-terminal TALEN fusions using FokI as a catalytic head (classical TALEN architecture) suffers major drawbacks limiting the fields of its possible applications. Indeed, the FokI catalytic head requires TALEN dimerization to be active, which requires two TAL monomers facing each other on the two opposite DNA strands to recompose an active molecule (Christian, Cermak et al., 2010). In addition, the N-terminus toward C-terminus orientation of a TAL has to follow the 5' toward 3' orientation of one DNA strand to allow binding ((Deng, Yan et al. 2012; Mak, Bradley et al. 2012)). More importantly, the targeted sequences have to start with a thymine base (T) for an effective binding by the first RVDs of the protein located at the N-terminal domain of the TAL (Boch, Scholze et al. 2009; Moscou and Bogdanove 2009). This "T" requirement significantly reduces the possibilities of targeting any nucleotide sequence into the genome.

Given the above requirements for targeting DNA sequences into the genome, the inventors have developed new TALEN scaffolds, which unexpectedly allow targeting a broader spectrum of nucleic acid sequences more easily to target than using classical TALEN architecture.

BRIEF SUMMARY OF THE INVENTION

In a general aspect, the present invention relates to Transcription Activator-Like Effector (TALE) monomers, to which are fused catalytic domains, especially into their N-terminals. These catalytic domains, when associated with a catalytic domain of another TAL monomer, form a chemical or enzyme entity that allows the processing of DNA. This processing may be to modify the structure of the DNA molecule by cleavage, base replacement or chemical reaction. It may be also to regulate gene expression.

Figure 4:
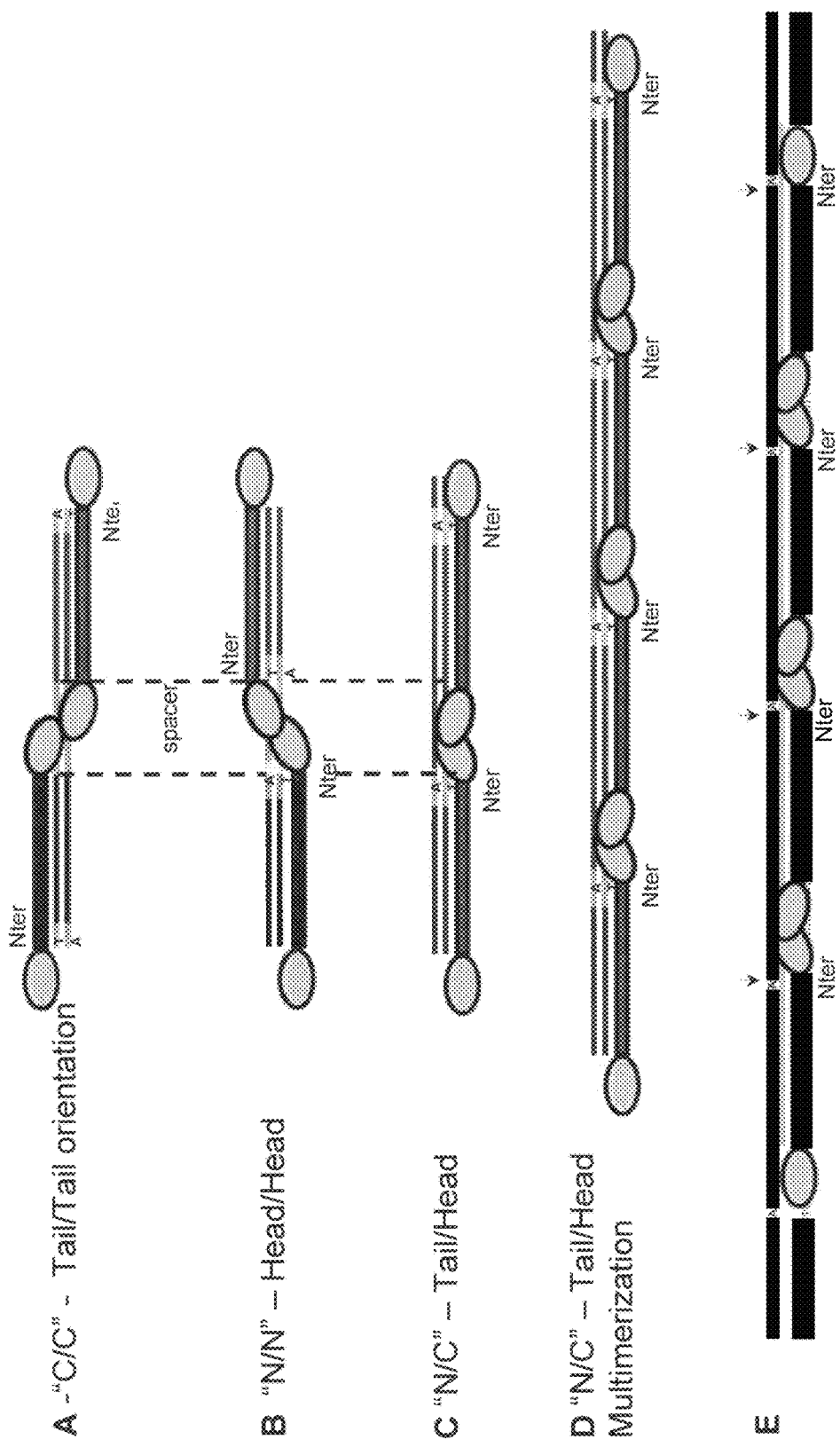
Figure 5:
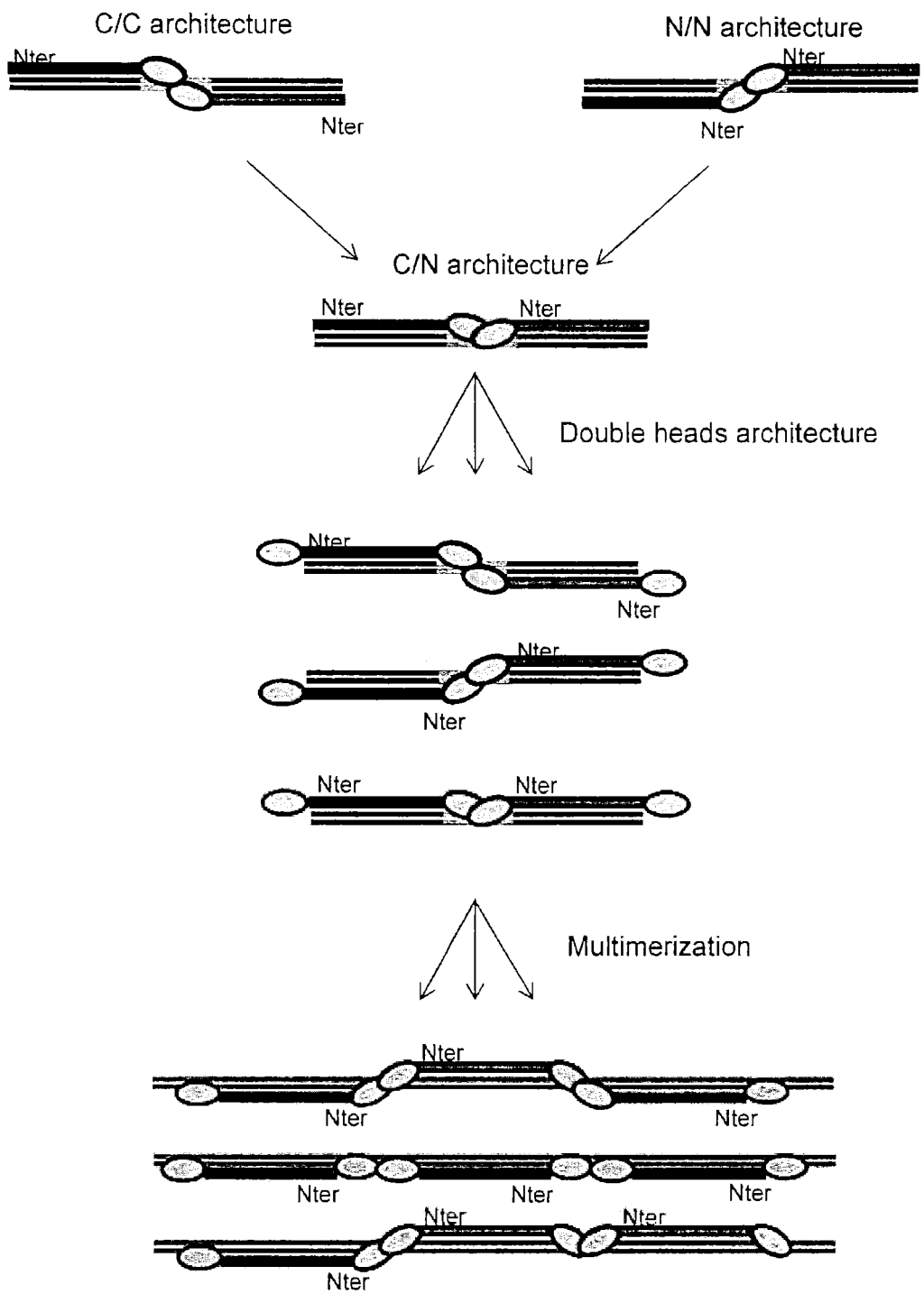

As a particular embodiment, the TAL-derived monomers have two catalytic domains respectively fused to their N and C-terminals, so that multiple monomers can be associated together all along a DNA sequence in order to create different catalytic entities intervening at different DNA locations, The catalytic entities become active preferably concomitantly, upon multimer formation upon binding to their respective DNA targets (FIGS. 4 and 5).

By contrast to the classical TALEN architecture, the polypeptides according to the invention, allow to efficiently target sequences that are all located on either DNA strand. In particular, they make possible to target only one DNA strand.

Also, the TAL-derived monomers according to the invention allow to target nucleic acid sequences that are not targetable with the classical TALEN architecture, especially double strand DNA sequences comprising fewer T bases or none on one strand, such as those composed of highly repetitive sequences of G, A and C triplets (e.g. expansion triplets).

The present invention also concerns different methods in which these polypeptides can be advantageously used, as well as nucleic acids and vectors encoding such polypeptides.

BRIEF DESCRIPTION OF THE FIGURES AND TABLES

In addition to the preceding features, the invention further comprises other features which will emerge from the description which follows, as well as to the appended drawings. A more complete appreciation of the invention and many of the attendant advantages thereof will be readily obtained as the same becomes better understood by reference to the following Figures in conjunction with the detailed description below.

FIG. 1: Prior Art. Schematic representation of the classical TALEN architecture as described in the international application WO2011/072246.

FIG. 2: Schematic representation of a new TALEN architecture according to the invention as described herein FIG. 3: Schematic of Head (N-terminal)/Tail (C-terminal) protein configuration according to the invention.

FIG. 4A-E: Schematic representation of different configurations made possible by associating several Tal derived monomers according to the invention. A—Tail/Tail orientation: The TAL monomers interact through their C-terminal fused catalytic domains, whereas there are binding to sequences located on each DNA strands. B—Head/Head orientation: The TAL monomers interact through their N-terminal fused catalytic domains. C—Tail/Head orientation: The TAL monomers interact through their N and C-terminal fused catalytic domains, while they are binding to target sequences that are located on the same DNA strand. D—Tail/Head multimerization: Several TAL monomers interact through their N and C-terminal fused catalytic domains, creating multiple catalytic entities, all the monomers being located on the same DNA strand. E—Same situation as in D, an example of DNA sequence (top strand is CAG repeats) is provided showing that the other DNA strand does not provide a T base, and therefore could not be targeted by using classical TALEN. T represents the base that must be present in the DNA target sequence for it to be properly recognized by the first RVD of the TAL binding domain.

FIG. 5: Double head architecture and example of TAL multimerization using the monomers according to the invention.

Table 1: Cleavage activity of Tail/Tail configuration (see example 1) on pseudo-palindromic sequences targets (two identical recognition sequences are placed facing each other on both DNA strands separated by a spacer ranging from 5 to 40 bps in our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006) at 37° C.+/− represent a barely detectable activity, +a low activity, ++a medium activity and +++a high activity. n.d. indicates that no activity was detected.

Table 2: Cleavage activity of Head/Head configuration (see example 1) on pseudo-palindromic sequences targets (two identical recognition sequences are placed facing each other on both DNA strands separated by a spacer ranging from 5 to 35 bps in our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006) at 37° C.+/− represent a barely detectable activity, +a low activity, ++a medium activity and +++a high activity. n.d. indicates that no activity was detected.

Table 3: Cleavage activity of Head/Tail configuration (see example 2) on either targets containing two identical GCT repeated sequences, on the same strand, separated by a spacer of 12, 15, 18, 21, 24, 27 or 30 bps or a target composed exclusively of GCT repetitions in our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006) at 37° C.+ represent a low activity, ++a medium activity and +++a high activity.

DETAILED DESCRIPTION OF THE INVENTION

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

In a general aspect, the present invention relates to polypeptides that allow to efficiently target and/or process nucleic acids.

In a particular aspect, the present invention relates to polypeptides derived from Transcription Activator-Like Effector derived proteins, under the form of chimeric proteins, having an improved design or architecture, which allows to efficiently target and/or process DNA sequences that are not targetable with the classical TALEN architecture.

According to a first embodiment, the invention provides monomers derived from a Transcription Activator-Like Effector (TALE) comprising a core scaffold comprising Repeat Variable Dipeptide regions (RVDs) having binding specificity to a DNA target sequence and a catalytic domain fused to the N-terminal of said core scaffold. This fusion is generally operated using an appropriate flexible peptide linker. Said catalytic domain is preferably chosen in relation to another catalytic domain fused to another TAL-derived monomer, called counterpart domain.

According to one aspect of the invention, this counterpart domain preferably interacts with the first catalytic domain, so as to form a catalytic entity. Said catalytic domain or said catalytic entity has the ability to process DNA, which means that it can have an activity on the physical structure of the DNA, like for instance a nuclease activity, or an effect on gene expression, like for instance by inhibiting or enhancing transcription.

As a preferred embodiment, nuclease activity is provided by said catalytic domain. As an example an enzyme having type IIS nuclease activity, such as FokI (SEQ ID NO.91) can be fused to the N-terminal of the TAL derived scaffold. Enzymes, like Fok1 have the advantage of being active under dimer form, so that a first FolkI monomer can be fused to the first TAL scaffold, and a second FolkI monomer to a second TAL scaffold, in order to form a FolkI homodimer as an active catalytic entity having nuclease activity. Such a catalytic domain comprises an amino acid sequence having at least 80%, preferably at least 90%, more preferably at least 95% identity with SEQ ID NO: 91.

As another example, monomers of endonucleases can be fused to TAL scaffolds, especially from meganucleases, to form a catalytic entity having nuclease activity. Thereby, the catalytic domain can be a monomer that will form a heterodimer or homodimer catalytic entity having nuclease activity, when put into contact with its counterpart.

A protein monomer according to the invention can also have a catalytic entity emitting a recordable reporter signal.

In agreement with what precedes, the invention is more particularly drawn to a monomer comprising:
  A core scaffold comprising Repeat Variable Dipeptide regions (RVDs) having binding specificity to a DNA target sequence; and
  At least two catalytic domains respectively fused to the N-terminal and C-terminals of said core scaffold, wherein at least one of said catalytic domain, when in contact with a counterpart catalytic domain, form a catalytic entity to process DNA, upstream or downstream of said target sequence.

According to such embodiment, the N-terminal and C-terminals are both fused with catalytic domains, which does not mean that both catalytic domains are identical or display the same activities.

According to another aspect of the invention, the counterpart domain does not directly interact with the catalytic domain, but contributes to an additional or a further step of the DNA processing. In such case, the activities of both catalytic domains can be simultaneous or take place at different times. Nevertheless, as per the invention, those different activities are drawn to the same DNA region preferably located between the target sequence of each TAL-derived monomers. For instance, the first catalytic domain can have an endonuclease activity on this region and the second catalytic domain can have a nikase, so that NHEJ activity on said DNA region is increased.

Since the catalytic domain generally derives from an enzyme, the polypeptides according to the invention can be a protein encoded by a nucleic acid or a vector encoding such a polypeptide, which are also part of the invention.

Compared to classical TALEN architecture based on AvrBs3, the polypeptides of the invention, which are preferably monomers, display a new structure by fusion of said catalytic domain to the N-terminal of a TAL derived scaffold. Such monomers according to the invention have the ability to form multimers which can bind to any DNA strand of a double stranded DNA. In particular, it can bind to only one strand of said double stranded DNA, which was not possible to the classical TALEN architecture. This possibility had not been previously foreseen because classical TALEN architecture has derived from the protein AvrBs3, which does not naturally comprise a catalytic domain in its N-terminal part. Also, in classical TALEN architecture, the nucleases have been so far fused to the C-terminal part of AvrBs3 in order to help or at least preserve dimerization of the whole protein.

Interestingly, it has been found by the present inventors that fusion to the N-terminal part of the TAL derived Scaffold could produce monomers that do not require dimerization of the core scaffold to be functional. Accordingly, when the catalytic domains are fused to the N-terminal part of the monomers, the core scaffolds may not need to assemble for obtaining an activity. Only the catalytic domains fused to the TAL derived scaffolds, should these catalytic domains have to dimerize to form an active catalytic entity (such as of FolkI), then need to dimerize. As a result, the TAL core scaffolds apparently undergo less steric constraints when they bind to target sequences, and thus, said target sequences can be defined on either DNA strand, which was not possible with classical TALEN architecture. According to a preferred method, the monomers bind to the same DNA strand.

Accordingly, the present invention more particularly concerns methods to process a double stranded DNA sequence into a cell by expressing the monomers previously described, and also methods combining such monomers to more efficiently target and process such DNA sequence. Several combinations of the monomers are illustrated in FIG. 4 to target and/or process double stranded DNA. Said methods typically comprise transfecting a cell with one or more polynucleotide(s) expressing one or several monomer(s) as previously defined.

As a preferred embodiment of the invention, the monomers are fused to catalytic domains inducing double strand break (DSB) into the DNA between the sequences targeted by the RVDs of said two monomers. By this way, the method of the invention can be used for modifying genomic DNA, and can comprise additional steps of genetic engineering, in particular steps using homologous recombination techniques.

This method is particularly suited when one of the two DNA strand sequences is devoid of T or comprises fewer T, making it difficult to target with classical TALEN.

Such a method generally comprises at least one of the following steps:
  Identifying said double stranded DNA sequence in a cell;
  Transfecting said cell with one or two nucleic acid encoding at least two protein monomers each comprising:

A core scaffold comprising Repeat Variable Dipeptide regions (RVDs) having binding specificity to a DNA target sequence on one strand of said double stranded DNA; and A catalytic domain; the catalytic domain of the first monomer being fused to the N-terminal of its core scaffold, and the catalytic domain of the second monomer being fused to the C-terminal of its core scaffold, said two catalytic domains, when they are in contact, forming a catalytic entity being able to process DNA between the respective target sequences of said two monomers.

expressing said protein monomers into said cell;

such that said monomers bind their respective target sequences and process DNA between said target sequences through the combination of their catalytic domains.

Preferably, the Repeat Variable Dipeptide regions (RVDs) of both monomers are chosen to bind target sequences, which are located on the same DNA strand, preferably the DNA strand that comprises more T bases than the other. It may happen, for instance, that a nucleic acid sequence can be devoid of T or show T only at inappropriate positions, making it more difficult to target using classical TALEN architecture. This may be the case in particular when it comprises multiple repeats or trinucleotide repeats expansion. A DNA sequence may also contain a low number of T bases in a genomic region to be processed, which then reduces the number of manageable targets. The method according to the invention aims to resolve such situations, by allowing to reaching more putative targets into a genome.

Accordingly, the method of the invention may include the steps of providing a cell containing a DNA sequence showing a low occurrence of T, generally less than 20%, more generally less than 10%, more generally less than 5%, and even less than 1 or 2%, in view of its processing as previously described.

Also, the method of the invention allow to process a double stranded DNA sequence comprising putative trinucleotide repeats expansion devoid of T; or displaying a lower occurrence of T on one of its strand, said method comprising at least one of the following steps:

Providing a cell which may contain a double stranded DNA sequence comprising such putative trinucleotide repeats expansion devoid of T on one of its strand;

Determining a threshold number of trinucleotide repeats under which no processing is desired;

Transfecting said cell with one or two nucleic acid encoding at least two protein monomers each comprising:

A core scaffold comprising Repeat Variable Dipeptide regions (RVDs) having binding specificity to said number of trinucleotide repeats; and A catalytic domain; the catalytic domain of the first monomer being fused to the N-terminal of its core scaffold, and the catalytic domain of the second monomer being fused to the C-terminal of its core scaffold, said two catalytic domains, when they are in contact, forming a catalytic entity being able to process DNA between the respective target sequences of said two monomers.

Inducing expression of said chimeric protein monomer encoded by said nucleic acid;

such that said protein monomers bind and process DNA between said trinucleotide repeats DNA target sequences when said repeats are equal or above said threshold number.

The activity of the above new TALEN monomers on multiple repeats is also tunable by modifying the number of RVDs (e.g. sequences containing a number of repetitions under a threshold value are protected from cleavage using TALEN containing long arrays of RVDs and in contrary short arrays of RVDs allows targeting smaller number of repetitions).

According to another aspect of the invention, the previously described monomers may be used in a method to measure the number of putative repeated sequences within a double stranded genome DNA sequence, in particular repeated sequences devoid of T on one strand of said genome sequence, said method comprising at least one of the following steps:

providing said DNA genome in a cell

Transfecting said cell with one or two nucleic acids encoding at least two protein monomers each comprising:

A core scaffold comprising Repeat Variable Dipeptide regions (RVDs) having binding specificity to said repeated DNA sequence (target sequence); and A catalytic domain; the catalytic domain of the first monomer being fused to the N-terminal of its core scaffold, and the catalytic domain of the second monomer being fused to the C-terminal of its core scaffold, said two catalytic domains, when they are in contact, forming a catalytic entity being able to produce a reporter signal.

Inducing expression of said protein monomers encoded by said nucleic acid(s);

Recording said reporter signal intensity;

Deducing from said reporter signal intensity the number of putative repeated sequences within said DNA sequence into the genome of said cell;

Optionally, comparing this reporter signal intensity with the reporter signal intensity recovered from a control cell.

The methods of the invention may be applied to any types of cells, especially eukaryotic cells including mammalian and plant cells.

The DNA to be processed is preferably chromosomal DNA. The invention could also be applied to other nucleic acids, such as RNA.

Considering the above methods, especially the multimerization process into which several monomers of the invention are used in combination, one aspect of the invention concerns a set or a kit of at least two protein monomers as previously defined. It also concerns kit of polynucleotides or vectors encoding such monomers.

In these sets or kits, said first and second monomers preferably comprise:

A core scaffold comprising Repeat Variable Dipeptide regions (RVDs) having binding specificity to a DNA target sequence; and A catalytic domain; the catalytic domain of the first monomer being fused to the N-terminal of its core scaffold, and the catalytic domain of the second monomer being fused to the C-terminal of its core scaffold, said two catalytic domains, when they are in contact, forming a catalytic entity being able to process DNA between the respective target sequences of said two monomers.

As previously mentioned, the DNA target sequences of said two monomers can be advantageously located on the same DNA strand of a given double stranded DNA.

Said set of kit can comprise additional monomers, especially a third monomer in order to bridge at least two, preferably at least three, target sequences, the number of monomers being in theory not limited. Numerous monomers may be used to ensure, for instance, the deletion or the silencing of a whole region in a genome. The present monomers may also be used to process methylated sequences, which are often more difficult to process. In particular, this may be used to increase the probability of DSB event in a region where the chromosomal DNA is difficult to access.

As an alternative, several monomers may be assembled into a single chain polypeptide, thereby being expressed by a single polynucleotide.

OTHER DEFINITIONS

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

DNA or nucleic acid processing activity refers to a particular or given enzymatic activity conferred by a catalytic domain onto the nucleic acid structure or onto the expression of genes, directly on indirectly. Said DNA or nucleic acid processing activity can refer to a cleavage activity, either a cleavase activity either a nickase activity, more broadly a nuclease activity but also a polymerase activity, a transcriptional activity, a kinase activity, a phosphatase activity, a methylase activity, a topoisomerase activity, an integrase activity, a transposase activity, a ligase, a helicase or recombinase activity as non-limiting examples.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

by "peptide linker" or "peptidic linker" it is intended to mean a peptide sequence which allows the connection of different monomers or different parts comprised in a fusion protein such as between a TALE DNA binding domain and a protein domain in a chimeric protein or a polypeptide according to the present invention and which allows the adoption of a correct conformation for said chimeric protein activity and/or specificity. Peptide linkers can be of various sizes, from 3 amino acids to 50 amino acids as a non limiting indicative range. Peptide linkers can also be qualified as structured or unstructured. Peptide linkers can be qualified as active linkers when they comprise active domains that are able to change their structural conformation under appropriate stimulation.

by "subdomain" it is intended a protein subdomain or a protein part that interacts with another protein subdomain or protein part to form an active entity and/or a catalytic active entity bearing nucleic acid or DNA processing activity of said chimeric protein or polypeptide according to the invention.

by "exogenous sequence" it is intended to mean a DNA construct comprising a first and second portion that are homologous to regions 5' and 3' of a DNA target in situ.

The DNA construct also comprises a third portion positioned between the first and second portion which comprise some homology with the corresponding DNA sequence in situ or alternatively comprise no homology with the regions 5' and 3' of the DNA target in situ. Following cleavage of the DNA target, a homologous recombination event is stimulated between the genome containing the targeted gene comprised in the locus of interest and the repair matrix, wherein the genomic sequence containing the DNA target is replaced by the third portion of the repair matrix and a variable part of the first and second portions of the repair matrix.

by "DNA target", "DNA target sequence", "target DNA sequence", "nucleic acid target sequence", "target sequence", is intended a polynucleotide sequence which can be bound by the TALE DNA binding domain that is included in the proteins of the present invention. It refers to a specific DNA location, preferably a genomic location in a cell, but also a portion of genetic material that can exist independently to the main body of genetic material such as plasmids, episomes, virus, transposons or in organelles such as mitochondria or chloroplasts as non-limiting examples. The nucleic acid target sequence is defined by the 5' to 3' sequence of one strand of said target, as indicated for SEQ ID NO: 83 to 89 in table 3 as a non-limiting example. Generally, the DNA target is adjacent or in the proximity of the locus to be processed either upstream (5' location) or downstream (3' location). In a preferred embodiment, the target sequences and the proteins are designed in order to have said locus to be processed located between two such target sequences. Depending on the catalytic domains of the proteins, the target sequences may be distant from 5 to 50 bases (bp), preferably from 10 to 40 bp, more preferably from 15 to 30, even more preferably from 15 to 25 bp. These later distances define the spacer referred to in the description and the examples. It can also define the distance between the target sequence and the nucleic acid sequence being processed by the catalytic domain on the same molecule.

By "delivery vector" or "delivery vectors" is intended any delivery vector which can be used in the present invention to put into cell contact (i.e "contacting") or deliver inside cells or subcellular compartments agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors. A vector according to the present invention comprises, but is not limited to, a YAC (yeast artificial chromosome), a BAC (bacterial artificial), a baculovirus vector, a phage, a phagemid, a cosmid, a viral vector, a plasmid, a RNA vector or a linear or circular DNA or RNA molecule which may consist of chromosomal, non chromosomal, semi-synthetic or synthetic DNA. In general, expression vectors of utility in recombinant DNA techniques are often in the form of "plasmids" which refer generally to circular double stranded DNA loops which, in their vector form are not bound to the chromosome. Large numbers of suitable vectors are known to those of skill in the art. Vectors can comprise selectable markers, for example: neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP1 for *S. cerevisiae*; tetracyclin, rifampicin or ampicillin resistance in *E. coli*. Preferably said vectors are expression vectors, wherein a sequence encoding a polypeptide of interest is placed under control of appropriate transcriptional and translational control elements to permit production or synthesis of said polypeptide. Therefore, said polynucleotide is comprised in an expression cassette. More particularly, the vector comprises a replication origin, a promoter operatively linked to said encoding polynucleotide, a ribosome binding site, a RNA-splicing site (when genomic DNA is used), a polyadenylation site and a transcription termination site. It also can comprise an enhancer or silencer elements. Selection of the promoter will depend upon the cell in which the polypeptide is expressed. Suitable promoters include tissue specific and/or inducible promoters. Examples of inducible promoters are: eukaryotic metallothionine promoter which is induced by increased levels of heavy metals, prokaryotic lacZ promoter which is induced in response to isopropyl-β-D-thiogalacto-pyranoside (IPTG) and eukaryotic heat shock promoter which is induced by increased temperature. Examples of tissue specific promoters are skeletal muscle creatine kinase, prostate-specific antigen (PSA), α-antitrypsin protease, human surfactant (SP) A and B proteins, β-casein and acidic whey protein genes. Delivery vectors and vectors can be associated or combined with any cellular permeabilization techniques such as sonoporation or electroporation or derivatives of these techniques.

Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells.

By "integrative lentiviral vectors (or LV)", is meant such vectors as non limiting example, that are able to integrate the genome of a target cell.

At the opposite by "non integrative lentiviral vectors (or NILV)" is meant efficient gene delivery vectors that do not integrate the genome of a target cell through the action of the virus integrase.

Inducible promoters may be induced by pathogens or stress, more preferably by stress like cold, heat, UV light, or high ionic concentrations (reviewed in Potenza C et al. 2004, In vitro Cell Dev Biol 40:1-22). Inducible promoter may be induced by chemicals (reviewed in (Moore, Samalova et al. 2006); (Padidam 2003); (Wang, Zhou et al. 2003); (Zuo and Chua 2000).

By cell or cells is intended any prokaryotic or eukaryotic living cells, cell lines derived from these organisms for in vitro cultures, primary cells from animal or plant origin.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines. These cells thus represent a more valuable model to the in vivo state they refer to.

In the frame of the present invention, "eukaryotic cells" refer to a fungal, plant or animal cell or a cell line derived from the organisms listed below and established for in vitro culture. More preferably, the fungus is of the genus *Aspergillus, Penicillium, Acremonium, Trichoderma, Chrysoporium, Mortierella, Kluyveromyces* or *Pichia*; More preferably, the fungus is of the species *Aspergillus niger, Aspergillus nidulans, Aspergillus oryzae, Aspergillus terreus, Penicillium chrysogenum, Penicillium citrinum, Acremonium Chrysogenum, Trichoderma reesei, Mortierella alpine, Chrysosporium lucknowense, Kluyveromyces lactis, Pichia pastoris* or *Pichia ciferrii*. More preferably the plant is of the genus *Arabidospis, Nicotiana, Solanum, lactuca, Brassica, Oryza,* Asparagus, *Pisum, Medicago, Zea, Hordeum, Secale, Triticum, Capsicum, Cucumis, Cucurbita, Citrullis, Citrus, Sorghum*; More preferably, the plant is of the species *Arabidospis*

*thaliana, Nicotiana tabaccum, Solanum lycopersicum, Solanum tuberosum, Solanum melongena, Solanum esculentum, Lactuca saliva, Brassica napus, Brassica oleracea, Brassica rapa, Oryza glaberrima, Oryza sativa, Asparagus officinalis, Pisum sativum, Medicago sativa, zea mays, Hordeum vulgare, Secale cereal, Triticum aestivum, Triticum durum, Capsicum sativus, Cucurbita pepo, Citrullus lanatus, Cucumis melo, Citrus aurantifolia, Citrus maxima, Citrus medica, Citrus reticulata.*

More preferably the animal cell is of the genus Homo, Rattus, Mus, Sus, Bos, Danio, Canis, Felis, Equus, Salmo, Oncorhynchus, Gallus, Meleagris, Drosophila, Caenorhabditis; more preferably, the animal cell is of the species *Homo sapiens, Rattus norvegicus, Mus musculus, Sus scrofa, Bos taurus, Danio rerio, Canis lupus, Felis catus, Equus caballus, Salmo salar, Oncorhynchus mykiss, Gallus gallus, Meleagris gallopavo, Drosophila melanogaster, Caenorhabditis elegans.*

In the present invention, the cell can be a plant cell, a mammalian cell, a fish cell, an insect cell or cell lines derived from these organisms for in vitro cultures or primary cells taken directly from living tissue and established for in vitro culture. As non limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells.

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

by "mutation" is intended the substitution, deletion, insertion of one or more nucleotides/amino acids in a polynucleotide (cDNA, gene) or a polypeptide sequence. Said mutation can affect the coding sequence of a gene or its regulatory sequence. It may also affect the structure of the genomic sequence or the structure/stability of the encoded mRNA.

In the frame of the present invention, the expression "double-strand break-induced mutagenesis" (DSB-induced mutagenesis) refers to a mutagenesis event consecutive to an NHEJ event following an endonuclease-induced DSB, leading to insertion/deletion at the cleavage site of an endonuclease.

By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.

As used herein, the term "locus" is the specific physical location of a DNA sequence (e.g. of a gene) on a chromosome. The term "locus" usually refers to the specific physical location of a polypeptide or chimeric protein's nucleic target sequence on a chromosome. Such a locus can comprise a target sequence that is recognized and/or cleaved by a polypeptide or a chimeric protein according to the invention. It is understood that the locus of interest of the present invention can not only qualify a nucleic acid sequence that exists in the main body of genetic material (i.e. in a chromosome) of a cell but also a portion of genetic material that can exist independently to said main body of genetic material such as plasmids, episomes, virus, transposons or in organelles such as mitochondria or chloroplasts as non-limiting examples.

By "fusion protein" is intended the result of a well-known process in the art consisting in the joining of two or more genes which originally encode for separate proteins or part of them, the translation of said "fusion gene" resulting in a single polypeptide with functional properties derived from each of the original proteins.

By "chimeric protein" according to the present invention is meant any fusion protein comprising at least one RVD to bind a nucleic acid sequence and one protein domain to process a nucleic acid target sequence within or adjacent to said bound nucleic acid sequence.

By "protein domain" is meant the nucleic acid target sequence processing part of said chimeric protein according to the present invention. Said protein domain can provide any catalytical activity (catalytic domain) as classified and named according to the reaction they catalyze [Enzyme Commission number (EC number) at chem.qmul.ac.uk/iubmb/enzyme/)]. Said protein domain can be a catalytically active entity by itself. Said protein domain can be a protein subdomain that needs to interact with another protein subdomain to form a dimeric protein domain active entity.

By a "TALE-nuclease" (TALEN) is intended a fusion protein consisting of a DNA-binding domain derived from a Transcription Activator Like Effector (TALE) and one nuclease catalytic domain to cleave a nucleic acid target sequence. Said TALEN is a subclass of chimeric protein according to the present invention.

By "variant(s)", it is intended a RVD variant, a chimeric protein variant, a DNA binding variant, a TALEN variant, a polypeptide variant obtained by replacement of at least one residue in the amino acid sequence of the parent molecule.

By "functional mutant" is intended a catalytically active mutant of a protein or a protein domain; such mutant can have the same activity compared to its parent protein or protein domain or additional properties. This definition applies to chimeric proteins or protein domains that constitute chimeric proteins according to the present invention. Are also encompassed in the scope of this definition "derivatives" of these proteins or protein domains that comprise the entirety or part of these proteins or protein domains fused to other proteic or chemical parts such as tags, antibodies, polyethylene glycol as non-limiting examples.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. Unless otherwise stated, the present invention encompasses polypeptides and polynucleotides sharing at least 70%, generally at least 80%, more generally at least 85%, preferably at least 90%, more preferably at least 95% and even more preferably at least 97% with those described herein.

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out. The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only.

EXAMPLES

Example 1

Activities of Tail/Tail and Head/Head Protein Configurations

Cloning of the "AvrBs3" RVD Array in the TAL Backbone

The amino acid sequences of the N-terminal, C-terminal domains and RVDS were based on the AvrBs3 TAL (ref: Gen Bank: X16130.1, SEQ ID NO: 1). The yeast expression TAL backbones used in these experiment (pCLS13597, SEQ ID NO: 2 and pCLS12843, SEQ ID NO: 3) were derived from the pCLS8422 (SEQ ID NO: 4) and pCLS8426 (SEQ ID NO: 5) respectively, where a second FokI Catalytic head was introduced by blunt end cloning in the EcoRV site and subsequent sequencing to validate the FokI orientation and sequence integrity. The cassette comprised between the NcoI and BamHI were further subcloned in pCLS7183 (SEQ ID NO: 6) leading to the final yeast cloning backbones. These backbone, pCLS13597 and pCLS12843, contain an additional N-terminal NLS sequence followed by an HA tag upstream the first FokI catalytic head. The C-terminal and the N-terminal domains (complete Nter domain, SEQ ID NO: 7, associated with pCLS12843 or delta152 truncated Nter, SEQ ID NO: 8, associated with pCLS13597) are separated by two BsmBI restriction sites. The RVD arrays (17.5 RVDs, SEQ ID NO: 9), targeting the AvrBs3 sequence (SEQ ID NO: 10) was assembled in solution by creation of the four tetra-RVDs (coding for blocks 1-4, 5-8, 9-12 and 13-16) from di-RVDs. The two octa-RVDs (1-8 and 9-16) were assembled starting from the four tetra-RVDs to form the hexadeca-RVD (1-16). The final RVD array was prepared by assembly of the hexadeca-RVD with the terminal 1.5 RVD block. All the assembly steps were done using restriction enzymes SfaNI and BbvI and T4 DNA ligase, following classical molecular biology protocols. The final array was then subcloned in both pCLS13597 and pCLS12843 using type IIs restriction enzymes BsmBI for the receiving plasmid and BbvI and SfaNI for the inserted RVD sequence leading to pCLS14333 (SEQ ID NO: 11) and pCLS12944 (SEQ ID NO: 12). DNA coding for the TAL was amplified in *E. coli*, recovered by standard miniprep techniques and sequenced to assess the integrity of the insert.

Activities in Yeast

The activity of the two individual FokI catalytic heads and their dependence toward the spacer length were tested at 37° C. and 30° C. in our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006) on pseudo-palindromic sequences; two identical recognition sequences are placed facing each other (Tail/Tail or Head/Head) on both DNA strands (SEQ ID NO: 16 to 51 (Tail/Tail) and 52 to 82 (Head/Head). All the yeast target reporter plasmids containing the TALEN DNA target sequences were constructed as previously described (International PCT Applications WO 2004/067736 and in (Epinat, Arnould et al. 2003; Chames, Epinat et al. 2005; Arnould, Chames et al. 2006; Smith, Grizot et al. 2006). TALEN cleavage activity levels, in yeast, of individual clones on the complete sets of targets are presented in table 1 (Tail/Tail) and table 2 (Head/Head).

Example 2

Activities of Head/Tail Protein Configuration

Cloning of the "GCT" RVD Array in the TAL Backbone

The amino acid sequences of the N-terminal, C-terminal domains and RVDS were based on the AvrBs3 TAL (ref: GenBank: X16130.1, SEQ ID NO: 1). The yeast expression TAL backbone used in these experiment (pCLS13597, SEQ ID NO: 2) was derived from the pCLS8422 (SEQ ID NO: 4), where a second FokI Catalytic head was introduced by blunt end cloning in the EcoRV site and subsequent sequencing to validate the FokI orientation and sequence integrity. The cassette comprised between the NcoI and BamHI was further subcloned in pCLS7183 (SEQ ID NO: 6) leading to the final cloning yeast backbone. This backbone, pCLS13597, contains an additional N-terminal NLS sequence followed by an HA tag upstream the first FokI catalytic head. The C-terminal and the N-terminal domains are separated by two BsmBI restriction sites. The RVD arrays (SEQ ID NO: 13), targeting the repeated GCT sequences (SEQ ID NO: 14) was synthesized using a solid support method composed of consecutive restriction/ligation/washing steps. In brief the first block (coding for a di-RVD) was immobilized on a solid support through biotin/streptavidin interaction, the second bloc (tri-RVD) is then ligated to the first and after SfaNI digestion a third bloc (tri-RVD) is coupled. The process is repeated using tri- or di-RVD blocs upon obtaining of the desired RVD array. The product is cloned in a classical pAPG10 cloning plasmid for amplification in *E. coli* and sequencing. The RVD array was then subcloned in the pCLS13597 using type IIs restriction enzymes BsmBI for the receiving plasmid and BbvI and SfaNI for the inserted RVD sequence leading to pCLS14332 (SEQ ID NO: 15).

DNA coding for the TAL was amplified in *E. coli*, recovered by standard miniprep techniques and sequenced to assess the integrity of the insert.

Activities in Yeast

The activity of the pCLS14332 construct were tested at 37° C. and 30° C. in our yeast SSA assay previously described (International PCT Applications WO 2004/067736 and in Epinat, Arnould et al. 2003; Chames, Epinat et al. 2005; Arnould, Chames et al. 2006; Smith, Grizot et al. 2006) either on targets containing two identical CTG repeated sequences on the complementary strand (5'-3'), corresponding to the CAG repetition on the coding strand, separated by a spacer of 12, 15, 18, 21, 24, 27 or 30 bps (SEQ ID NO: 83 to 90) or a target composed exclusively of CTG repetitions on the complementary strand (5'-3'), corresponding to the CAG repetition on the coding strand, (SEQ ID NO: 90). All the yeast target reporter plasmids containing the TALEN DNA target sequences were constructed as previously described (International PCT Applications WO 2004/067736 and in (Epinat, Arnould et al. 2003; Chames, Epinat et al. 2005; Arnould, Chames et al. 2006; Smith, Grizot et al. 2006). TALEN cleavage activity levels, in yeast, of individual clones on the complete set of targets are presented in table 3.

LIST OF CITED REFERENCES

Boch, J., H. Scholze, et al. (2009). "Breaking the code of DNA binding specificity of TAL-type III effectors." Science 326(5959): 1509-12.
Cermak, T., E. L. Doyle, et al. (2011). "Efficient design and assembly of custom TALEN and other TAL effector-based constructs for DNA targeting." Nucleic Acids Res 39(12): e82.
Christian, M., T. Cermak, et al. (2010). "Targeting DNA double-strand breaks with TAL effector nucleases." Genetics 186(2): 757-61.
Deng, D., C. Yan, et al. (2012). "Structural basis for sequence-specific recognition of DNA by TAL effectors." Science 335(6069): 720-3.
Geissler, R., H. Scholze, et al. (2011). "Transcriptional activators of human genes with programmable DNA-specificity." PLoS One 6(5): e19509.
Huang, P., A. Xiao, et al. (2011). "Heritable gene targeting in zebrafish using customized TALENs." Nat Biotechnol 29(8): 699-700.
Kay S. et al. (2007). "A bacterial Effector Acts as a Plant Transcription factor and Induces a Cell Size Regulator." Science 318:648-651.
Li, L., M. J. Piatek, et al. (2012). "Rapid and highly efficient construction of TALE-based transcriptional regulators and nucleases for genome modification." Plant Mol Biol 78(4-5): 407-16.
Li, T., S. Huang, et al. (2010). "TAL nucleases (TALNs): hybrid proteins composed of TAL effectors and FokI DNA-cleavage domain." Nucleic Acids Res 39(1): 359-72.
Li, T., S. Huang, et al. (2011). "Modularly assembled designer TAL effector nucleases for targeted gene knockout and gene replacement in eukaryotes." Nucleic Acids Res 39(14): 6315-25.
Mahfouz, M. M., L. Li, et al. (2012). "Targeted transcriptional repression using a chimeric TALE-SRDX repressor protein." Plant Mol Biol 78(3): 311-21.
Mahfouz, M. M., L. Li, et al. (2011). "De novo-engineered transcription activator-like effector (TALE) hybrid nuclease with novel DNA binding specificity creates double-strand breaks." Proc Natl Acad Sci USA 108(6): 2623-8.
Mak, A. N., P. Bradley, et al. (2012). "The crystal structure of TAL effector PthXo1 bound to its DNA target." Science 335(6069): 716-9.
Miller, J. C., S. Tan, et al. (2011). "A TALE nuclease architecture for efficient genome editing." Nat Biotechnol 29(2): 143-8.
Morbitzer, R., J. Elsaesser, et al. (2011). "Assembly of custom TALE-type DNA binding domains by modular cloning." Nucleic Acids Res 39(13): 5790-9.
Moscou, M. J. and A. J. Bogdanove (2009). "A simple cipher governs DNA recognition by TAL effectors." Science 326(5959): 1501.
Mussolino, C., R. Morbitzer, et al. (2011). "A novel TALE nuclease scaffold enables high genome editing activity in combination with low toxicity." Nucleic Acids Res 39(21): 9283-93.
Sander, J. D., L. Cade, et al. (2011). "Targeted gene disruption in somatic zebrafish cells using engineered TALENs." Nat Biotechnol 29(8): 697-8.
Tesson, L., C. Usal, et al. (2011). "Knockout rats generated by embryo microinjection of TALENs." Nat Biotechnol 29(8): 695-6.
Weber, E., R. Gruetzner, et al. (2011). "Assembly of designer TAL effectors by Golden Gate cloning." PLoS One 6(5): e19722.
Zhang, F., L. Cong, et al. (2011). "Efficient construction of sequence-specific TAL effectors for modulating mammalian transcription." Nat Biotechnol 29(2): 149-53.

TABLE 1

| | Tail/Tail orientation | |
|---|---|---|
| spacer [bp] | pCLS12944 | pCLS14333 |
| 5 | +/− | n.d. |
| 6 | + | n.d. |
| 7 | n.d. | n.d. |
| 8 | + | +/− |
| 9 | ++ | + |
| 10 | +++ | +++ |
| 11 | +++ | +++ |
| 12 | +++ | +++ |
| 13 | +++ | +++ |
| 14 | +++ | +++ |
| 15 | +++ | +++ |
| 16 | +++ | +++ |
| 17 | +++ | +++ |
| 18 | +++ | +++ |
| 19 | +++ | +++ |
| 20 | +++ | +++ |
| 21 | +++ | +++ |
| 22 | +++ | +++ |
| 23 | +++ | +++ |
| 24 | +++ | +++ |
| 25 | +++ | +++ |
| 26 | +++ | +++ |
| 27 | +++ | +++ |
| 28 | +++ | +++ |
| 29 | +++ | +++ |
| 30 | +++ | +++ |
| 31 | +++ | +++ |
| 32 | +++ | +++ |
| 33 | +++ | +++ |
| 34 | +++ | +++ |
| 35 | +++ | +++ |
| 36 | +++ | +++ |
| 37 | +++ | ++ |
| 38 | +++ | + |
| 39 | +++ | + |
| 40 | +++ | n.d. |

TABLE 2

Head/Head orientation

| spacer [bp] | pCLS12944 | pCLS14333 |
|---|---|---|
| 5 | ++ | n.d. |
| 6 | ++ | n.d. |
| 7 | ++ | n.d. |
| 8 | ++ | n.d. |
| 9 | ++ | n.d. |
| 10 | ++ | n.d. |
| 11 | ++ | n.d. |
| 12 | ++ | n.d. |
| 13 | ++ | n.d. |
| 14 | ++ | n.d. |
| 15 | +/− | n.d. |
| 16 | + | +/− |
| 17 | + | +/− |
| 18 | + | +/+ |
| 19 | + | +/+ |
| 20 | + | +/+ |
| 21 | + | ++ |
| 22 | + | +++ |
| 23 | + | +++ |
| 24 | n.d. | +++ |
| 25 | +/− | +++ |
| 26 | n.d. | +++ |
| 27 | +/− | +++ |
| 28 | +/− | 0, 8 |
| 29 | n.d. | n.d. |
| 30 | n.d. | n.d. |
| 31 | + | n.d. |
| 32 | n.d. | n.d. |
| 33 | +/− | ++ |
| 34 | +/− | +++ |
| 35 | +/− | +++ |

TABLE 3

| | pCLS14332 |
|---|---|
| TiCAG | +++ |
| TiCAG_sp12 | + |
| TiCAG_sp15 | ++ |
| TiCAG_sp18 | +++ |
| TiCAG_sp21 | +++ |
| TiCAG_sp24 | +++ |
| TiCAG_sp27 | +++ |
| TiCAG_sp30 | +++ |

The invention claimed is:

1. A method to process a double stranded DNA sequence comprising:
   (a) identifying the double stranded DNA sequence in a cell;
   (b) transfecting the cell with one or two nucleic acids encoding at least two protein monomers, wherein each of the protein monomers comprises:
      i) a Transcription Activator-Like Effector (TALE) core scaffold comprising Repeat Variable Dipeptide regions (RVDs) having binding specificity to a DNA target sequence and comprising amino acids 1-135 of SEQ ID NO:8 N-terminal to the RVDs,
      wherein the core scaffold is truncated at its N terminus such that it lacks the first 152 amino acids of SEQ ID NO:7; and
      ii) a nuclease catalytic domain of FokI;
   wherein the nuclease catalytic domain of FokI of the first monomer is fused to the N-terminus of the core scaffold, while the nuclease catalytic domain of FokI of the second monomer is fused to the C-terminus of its core scaffold,
   wherein the two catalytic domains, when they are in contact, form a catalytic entity that cleaves DNA between the respective target sequences of said two monomers;
   and wherein the DNA target sequences of the two monomers are located on the same DNA strand of the double stranded DNA and are separated by a spacer of 18-30 nucleotides; and
   (c) expressing the protein monomers in the cell such that the monomers bind their respective target sequences and cleave the DNA between the DNA target sequences by contacting their catalytic domains.

2. The method of claim 1, wherein the cell is a eukaryotic cell.

3. The method of claim 1, wherein the cell is a mammalian cell.

4. The method of claim 1, wherein the cell is a plant cell.

5. The method of claim 1, wherein the catalytic domains generate a double strand break in the DNA.

6. The method of claim 1, wherein the DNA is a chromosomal sequence.

7. The method of claim 1, wherein the DNA is an episomal sequence.

8. The method of claim 1, wherein the DNA is an organelle sequence.

9. The method of claim 1, comprising transfecting the cell with one nucleic acid encoding the at least two protein monomers.

10. The method of claim 1, comprising transfecting the cell with two nucleic acids, each encoding one of said protein monomers.

11. The method of claim 1, wherein the double stranded DNA is devoid of T on one of its DNA strands within the DNA target sequences and said Repeat Variable Dipeptide regions (RVDs) are chosen to bind target sequences that are located on the complementary DNA strand comprising T bases.

12. A method to process a double stranded DNA sequence comprising:
(a) identifying the double stranded DNA sequence in a cell;
(b) transfectinq the cell with one or two nucleic acids encoding at least two protein monomers, wherein each of the protein monomers comprises:
i) a Transcription Activator-Like Effector (TALE) core scaffold comprising Repeat Variable Dipeptide regions (RVDs) having binding specificity to a DNA target sequence and comprising amino acids 1-135 of SEQ ID NO:8 N-terminal to the RVDs,
wherein the core scaffold is truncated at its N terminus such that it lacks the first 152 amino acids of SEQ ID NO:7; and
ii) a nuclease catalytic domain of FolkI;
wherein the nuclease catalytic domain of FolkI of the first monomer is fused to the N-terminus of the core scaffold, while the nuclease catalytic domain of FolkI of the second monomer is fused to the C-terminus of its core scaffold,
wherein the two catalytic domains, when they are in contact, form a catalytic entity that cleaves DNA between the respective target sequences of said two monomers;
and wherein the DNA target sequences of the two monomers are located on the same DNA strand of the double stranded DNA and are separated by a spacer of 18-30 nucleotides; and
expressing the protein monomers in the cell such that the monomers bind their respective target sequences and cleave the DNA between the DNA target sequences by contacting their catalytic domains,
wherein the nuclease catalytic domain of FolkI of the second monomer comprises the amino acid sequence of SEQ ID NO:91.

* * * * *

SEQUENCE LISTING

<160> NUMBER OF SEQ ID NOS: 91

<210> SEQ ID NO 1
<211> LENGTH: 1164
<212> TYPE: PRT
<213> ORGANISM: Xanthomonas oryzae

<400> SEQUENCE: 1

```
Met Asp Pro Ile Arg Ser Arg Thr Pro Ser Pro Ala Arg Glu Leu Leu
1               5                   10                  15

Pro Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Ala Pro Ser Pro Ala Phe
    50                  55                  60

Ser Ala Gly Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Pro Thr Met Arg Val Ala Val Thr Ala Ala
        115                 120                 125

Arg Pro Pro Arg Ala Lys Pro Ala Pro Arg Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190
```

```
Ile Val Ala Leu Ser Gln His Pro Ala Ala Leu Gly Thr Val Ala Val
            195                 200                 205

Lys Tyr Gln Asp Met Ile Ala Ala Leu Pro Glu Ala Thr His Glu Ala
210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
            245                 250                 255

Thr Gly Gln Leu Leu Lys Ile Ala Lys Arg Gly Gly Val Thr Ala Val
            260                 265                 270

Glu Ala Val His Ala Trp Arg Asn Ala Leu Thr Gly Ala Pro Leu Asn
            275                 280                 285

Leu Thr Pro Glu Gln Val Val Ala Ile Ala Ser His Asp Gly Gly Lys
            290                 295                 300

Gln Ala Leu Glu Thr Val Gln Arg Leu Leu Pro Val Leu Cys Gln Ala
305                 310                 315                 320

His Gly Leu Thr Pro Gln Gln Val Val Ala Ile Ala Ser Asn Gly Gly
            325                 330                 335

Gly Lys Gln Ala Leu Glu Thr Val Gln Arg Leu Leu Pro Val Leu Cys
            340                 345                 350

Gln Ala His Gly Leu Thr Pro Gln Gln Val Val Ala Ile Ala Ser Asn
            355                 360                 365

Ser Gly Gly Lys Gln Ala Leu Glu Thr Val Gln Arg Leu Leu Pro Val
            370                 375                 380

Leu Cys Gln Ala His Gly Leu Thr Pro Glu Gln Val Val Ala Ile Ala
385                 390                 395                 400

Ser Asn Gly Gly Gly Lys Gln Ala Leu Glu Thr Val Gln Arg Leu Leu
                    405                 410                 415

Pro Val Leu Cys Gln Ala His Gly Leu Thr Pro Glu Gln Val Val Ala
            420                 425                 430

Ile Ala Ser Asn Ile Gly Gly Lys Gln Ala Leu Glu Thr Val Gln Ala
            435                 440                 445

Leu Leu Pro Val Leu Cys Gln Ala His Gly Leu Thr Pro Glu Gln Val
            450                 455                 460

Val Ala Ile Ala Ser Asn Ile Gly Gly Lys Gln Ala Leu Glu Thr Val
465                 470                 475                 480

Gln Ala Leu Leu Pro Val Leu Cys Gln Ala His Gly Leu Thr Pro Glu
                    485                 490                 495

Gln Val Val Ala Ile Ala Ser Asn Ile Gly Gly Lys Gln Ala Leu Glu
                500                 505                 510

Thr Val Gln Ala Leu Leu Pro Val Leu Cys Gln Ala His Gly Leu Thr
            515                 520                 525

Pro Glu Gln Val Val Ala Ile Ala Ser His Asp Gly Gly Lys Gln Ala
            530                 535                 540

Leu Glu Thr Val Gln Arg Leu Leu Pro Val Leu Cys Gln Ala His Gly
545                 550                 555                 560

Leu Thr Pro Glu Gln Val Val Ala Ile Ala Ser His Asp Gly Gly Lys
            565                 570                 575

Gln Ala Leu Glu Thr Val Gln Arg Leu Leu Pro Val Leu Cys Gln Ala
            580                 585                 590

His Gly Leu Thr Pro Gln Gln Val Val Ala Ile Ala Ser Asn Gly Gly
            595                 600                 605
```

-continued

Gly Lys Gln Ala Leu Glu Thr Val Gln Arg Leu Leu Pro Val Leu Cys
610                615                620

Gln Ala His Gly Leu Thr Pro Glu Gln Val Val Ala Ile Ala Ser Asn
625                630                635                640

Ser Gly Gly Lys Gln Ala Leu Glu Thr Val Gln Ala Leu Leu Pro Val
            645                650                655

Leu Cys Gln Ala His Gly Leu Thr Pro Glu Gln Val Val Ala Ile Ala
        660                665                670

Ser Asn Ser Gly Gly Lys Gln Ala Leu Glu Thr Val Gln Arg Leu Leu
            675                680                685

Pro Val Leu Cys Gln Ala His Gly Leu Thr Pro Glu Gln Val Val Ala
690                695                700

Ile Ala Ser His Asp Gly Gly Lys Gln Ala Leu Glu Thr Val Gln Arg
705                710                715                720

Leu Leu Pro Val Leu Cys Gln Ala His Gly Leu Thr Pro Glu Gln Val
                725                730                735

Val Ala Ile Ala Ser His Asp Gly Gly Lys Gln Ala Leu Glu Thr Val
            740                745                750

Gln Arg Leu Leu Pro Val Leu Cys Gln Ala His Gly Leu Thr Pro Glu
        755                760                765

Gln Val Val Ala Ile Ala Ser His Asp Gly Gly Lys Gln Ala Leu Glu
            770                775                780

Thr Val Gln Arg Leu Leu Pro Val Leu Cys Gln Ala His Gly Leu Thr
785                790                795                800

Pro Gln Gln Val Val Ala Ile Ala Ser Asn Gly Gly Arg Pro Ala
                805                810                815

Leu Glu Thr Val Gln Arg Leu Leu Pro Val Leu Cys Gln Ala His Gly
            820                825                830

Leu Thr Pro Glu Gln Val Val Ala Ile Ala Ser His Asp Gly Gly Lys
        835                840                845

Gln Ala Leu Glu Thr Val Gln Arg Leu Leu Pro Val Leu Cys Gln Ala
850                855                860

His Gly Leu Thr Pro Gln Gln Val Val Ala Ile Ala Ser Asn Gly Gly
865                870                875                880

Gly Arg Pro Ala Leu Glu Ser Ile Val Ala Gln Leu Ser Arg Pro Asp
            885                890                895

Pro Ala Leu Ala Ala Leu Thr Asn Asp His Leu Val Ala Leu Ala Cys
        900                905                910

Leu Gly Gly Arg Pro Ala Leu Asp Ala Val Lys Lys Gly Leu Pro His
            915                920                925

Ala Pro Ala Leu Ile Lys Arg Thr Asn Arg Arg Ile Pro Glu Arg Thr
930                935                940

Ser His Arg Val Ala Asp His Ala Gln Val Val Arg Val Leu Gly Phe
945                950                955                960

Phe Gln Cys His Ser His Pro Ala Gln Ala Phe Asp Asp Ala Met Thr
            965                970                975

Gln Phe Gly Met Ser Arg His Gly Leu Leu Gln Leu Phe Arg Arg Val
        980                985                990

Gly Val Thr Glu Leu Glu Ala Arg Ser Gly Thr Leu Pro Pro Ala Ser
            995                1000               1005

Gln Arg Trp Asp Arg Ile Leu Gln Ala Ser Gly Met Lys Arg Ala
        1010               1015               1020

```
Lys Pro Ser Pro Thr Ser Thr Gln Thr Pro Asp Gln Ala Ser Leu
    1025                1030                1035

His Ala Phe Ala Asp Ser Leu Glu Arg Asp Leu Asp Ala Pro Ser
    1040                1045                1050

Pro Met His Glu Gly Asp Gln Thr Arg Ala Ser Ser Arg Lys Arg
    1055                1060                1065

Ser Arg Ser Asp Arg Ala Val Thr Gly Pro Ser Ala Gln Gln Ser
    1070                1075                1080

Phe Glu Val Arg Val Pro Glu Gln Arg Asp Ala Leu His Leu Pro
    1085                1090                1095

Leu Ser Trp Arg Val Lys Arg Pro Arg Thr Ser Ile Gly Gly Gly
    1100                1105                1110

Leu Pro Asp Pro Gly Thr Pro Thr Ala Ala Asp Leu Ala Ala Ser
    1115                1120                1125

Ser Thr Val Met Arg Glu Gln Asp Glu Asp Pro Phe Ala Gly Ala
    1130                1135                1140

Ala Asp Asp Phe Pro Ala Phe Asn Glu Glu Glu Leu Ala Trp Leu
    1145                1150                1155

Met Glu Leu Leu Pro Gln
    1160

<210> SEQ ID NO 2
<211> LENGTH: 1893
<212> TYPE: DNA
<213> ORGANISM: artificial sequence
<220> FEATURE:
<223> OTHER INFORMATION: synthetic polynucleotide: pCLS13597

<400> SEQUENCE: 2
atgggcgatc ctaaaaagaa acgtaaggtc atcgattacc catacgatgt tccagattac      60
gctatcgata tccagctggt gaagtccgag ctggaggaga agaaatccga gttgaggcac     120
aagctgaagt acgtgcccca cgagtacatc gagctgatcg agatcgcccg gaacagcacc     180
caggaccgta tcctggagat gaaggtgatg gagttcttca tgaaggtgta cggctacagg     240
ggcaagcacc tgggcggctc caggaagccc gacggcgcca tctacaccgt gggctccccc     300
atcgactacg gcgtgatcgt ggacaccaag gcctactccg gcggctacaa cctgcccatc     360
ggccaggccg acgaaatgca gaggtacgtg gaggagaacc agaccaggaa caagcacatc     420
aaccccaacg agtggtggaa ggtgtacccc tccagcgtga ccgagttcaa gttcctgttc     480
gtgtccggcc acttcaaggg caactacaag gcccagctga ccaggctgaa ccacatcacc     540
aactgcaacg gcgccgtgct gtccgtggag gagctcctga tcggcggcga gatgatcaag     600
gccggcaccc tgaccctgga ggaggtgagg aggaagttca acaacggcga gatcaacttc     660
gctagctctg gaggttcagg ttctacggct gggtttatcg ccgatctacg cacgctcggc     720
tacagccagc agcaacagga gaagatcaaa ccgaaggttc gttcgacagt ggcgcagcac     780
cacgaggcac tggtcggcca cgggtttaca cacgcgcaca tcgttgcgtt aagccaacac     840
ccggcagcgt tagggaccgt cgctgtcaag tatcaggaca tgatcgcagc gttgccagag     900
gcgacacacg aagcgatcgt tggcgtcggc aaacagtggt ccggcgcacg cgctctggag     960
gccttgctca cggtggcggg agagttgaga ggtccaccgt tacagttgga cacaggccaa    1020
cttctcaaga ttgcaaaacg tggcggcgtg accgcagtgg aggcagtgca tgcatggcgc    1080
aatgcactga cgggtgcccc gctcaacttg accgagacg cccggggat caggtcacgt    1140 gcgtctcgga gcattgttgc ccagttatct cgccctgatc cggcgttggc cgcgttgacc    1200
```

| | |
|---|---|
| aacgaccacc tcgtcgcctt ggcctgcctc ggcgggcgtc ctgcgctgga tgcagtgaaa | 1260 |
| aagggattgg gggatcctat cagccgttcc cagctggtga agtccgagct ggaggagaag | 1320 |
| aaatccgagt tgaggcacaa gctgaagtac gtgccccacg agtacatcga gctgatcgag | 1380 |
| atcgcccgga acagcaccca ggaccgtatc ctggagatga aggtgatgga gttcttcatg | 1440 |
| aaggtgtacg gctacagggg caagcacctg ggcggctcca ggaagcccga cggcgccatc | 1500 |
| tacaccgtgg gctcccccat cgactacggc gtgatcgtgg acaccaaggc ctactccggc | 1560 |
| ggctacaacc tgcccatcgg ccaggccgac gaaatgcaga ggtacgtgga ggagaaccag | 1620 |
| accaggaaca agcacatcaa ccccaacgag tggtggaagg tgtacccctc cagcgtgacc | 1680 |
| gagttcaagt tcctgttcgt gtccggccac ttcaagggca actacaaggc ccagctgacc | 1740 |
| aggctgaacc acatcaccaa ctgcaacggc gccgtgctgt ccgtggagga gctcctgatc | 1800 |
| ggcggcgaga tgatcaaggc cggcaccctg accctggagg aggtgaggag gaagttcaac | 1860 |
| aacggcgaga tcaacttcgc ggccgactga taa | 1893 |

<210> SEQ ID NO 3
<211> LENGTH: 2349
<212> TYPE: DNA
<213> ORGANISM: artificial sequence
<220> FEATURE:
<223> OTHER INFORMATION: synthetic polynucleotide: pCLS12843

<400> SEQUENCE: 3

| | |
|---|---|
| atgggcgatc ctaaaaagaa acgtaaggtc atcgattacc catacgatgt tccagattac | 60 |
| gctatcgata tccagctggt gaagtccgag ctggaggaga gaaatccga gttgaggcac | 120 |
| aagctgaagt acgtgcccca cgagtacatc gagctgatcg agatcgcccg gaacagcacc | 180 |
| caggaccgta tcctggagat gaaggtgatg gagttcttca tgaaggtgta cggctacagg | 240 |
| ggcaagcacc tgggcggctc caggaagccc gacggcgcca tctacaccgt gggctccccc | 300 |
| atcgactacg gcgtgatcgt ggacaccaag gcctactccg gcggctacaa cctgcccatc | 360 |
| ggccaggccg acgaaatgca gaggtacgtg gaggagaacc agaccaggaa caagcacatc | 420 |
| aaccccaacg agtggtggaa ggtgtacccc tccagcgtga ccgagttcaa gttcctgttc | 480 |
| gtgtccggcc acttcaaggg caactacaag gcccagctga ccaggctgaa ccacatcacc | 540 |
| aactgcaacg gcgccgtgct gtccgtggag gagctcctga tcggcggcga gatgatcaag | 600 |
| gccggcaccc tgaccctgga ggaggtgagg aggaagttca caacggcga gatcaacttc | 660 |
| gctagctctg gaggttcagg ttctacggct gggtttatcg ccgaccccat cgttcgcgc | 720 |
| acaccaagtc ctgcccgcga gcttctgccc ggaccccaac ccgatggggt tcagccgact | 780 |
| gcagatcgtg gggtgtctcc gcctgccggc ggcccctgg atggcttgcc ggctcggcgg | 840 |
| acgatgtccc ggacccggct gccatctccc cctgccccct cacctgcgtt ctcggcgggc | 900 |
| agcttcagtg acctgttacg tcagttcgat ccgtcacttt ttaatacatc gcttttgat | 960 |
| tcattgcctc ccttcggcgc tcaccataca gaggctgcca caggcgagtg ggatgaggtg | 1020 |
| caatcgggtc tgcgggcagc cgacgccccc ccacccacca tgcgcgtggc tgtcactgcc | 1080 |
| gcgcggcccc cgcgcgccaa gccggcgccg cgacgacgtg ctgcgcaacc ctccgacgct | 1140 |
| tcgccggcgg cgcaggtgga tctacgcacg ctcggctaca gccagcagca acaggagaag | 1200 |
| atcaaaccga aggttcgttc gacagtggcc cagcaccacg aggcactggt cggccacggg | 1260 |
| tttacacacg cgcacatcgt tgcgttaagc caacacccgg cagcgttagg gaccgtcgct | 1320 |
| gtcaagtatc aggacatgat cgcagcgttg ccagaggcga cacacgaagc gatcgttggc | 1380 |

```
gtcggcaaac agtggtccgg cgcacgcgct ctggaggcct tgctcacggt ggcgggagag    1440
ttgagaggtc caccgttaca gttggacaca ggccaacttc tcaagattgc aaaacgtggc    1500
ggcgtgaccg cagtggaggc agtgcatgca tggcgcaatg cactgacggg tgccccgctc    1560
aacttgaccg gagacgcccg ggggatcagg tcacgtgcgt ctcggagcat tgttgcccag    1620
ttatctcgcc ctgatccggc gttggccgcg ttgaccaacg accacctcgt cgccttggcc    1680
tgcctcggcg gcgtcctgc gctggatgca gtgaaaaagg gattgggggga tcctatcagc    1740 cgttcccagc tggtgaagtc cgagctggag gagaagaaat ccgagttgag cacaagctg    1800 aagtacgtgc cccacgagta catcgagctg atcgagatcg cccggaacag cacccaggac    1860
cgtatcctgg agatgaaggt gatggagttc ttcatgaagg tgtacggcta caggggcaag    1920
cacctgggcg gctccaggaa gcccgacggc gccatctaca ccgtgggctc ccccatcgac    1980
tacggcgtga tcgtggacac caaggcctac tccggcggct acaacctgcc catcggccag    2040
gccgacgaaa tgcagaggta cgtggaggag aaccagacca ggaacaagca catcaacccc    2100
aacgagtggt ggaaggtgta ccccctccagc gtgaccgagt tcaagttcct gttcgtgtcc    2160
ggccacttca agggcaacta caaggcccag ctgaccaggc tgaaccacat caccaactgc    2220
aacggcgccg tgctgtccgt ggaggagctc ctgatcggcg gcgagatgat caaggccggc    2280
accctgaccc tggaggaggt gaggaggaag ttcaacaacg gcgagatcaa cttcgcggcc    2340
gactgataa                                                            2349
```

<210> SEQ ID NO 4
<211> LENGTH: 1260
<212> TYPE: DNA
<213> ORGANISM: artificial sequence
<220> FEATURE:
<223> OTHER INFORMATION: synthetic polynucleotide: pCLS8422

<400> SEQUENCE: 4

```
atgggcgatc ctaaaaagaa acgtaaggtc atcgattacc catacgatgt tccagattac      60
gctatcgata tcgccgatct acgcacgctc ggctacagcc agcagcaaca ggagaagatc     120
aaaccgaagg ttcgttcgac agtggcgcag caccacgagg cactggtcgg ccacgggttt     180
acacacgcgc acatcgttgc gttaagccaa cacccggcag cgttagggac cgtcgctgtc     240
aagtatcagg acatgatcgc agcgttgcca gaggcgacac acgaagcgat cgttggcgtc     300
ggcaaacagt ggtccggcgc acgcgctctg gaggccttgc tcacggtggc gggagagttg     360
agaggtccac cgttacagtt ggacacaggc caacttctca agattgcaaa acgtggcggc     420
gtgaccgcag tggaggcagt gcatgcatgg cgcaatgcac tgacgggtgc cccgctcaac     480
ttgaccggag acgccgggg gatcaggtca cgtgcgtctc ggagcattgt tgcccagtta     540
tctcgccctg atccggcgtt ggccgcgttg accaacgacc acctcgtcgc cttggcctgc     600
ctcggcgggc gtcctgcgct ggatgcagtg aaaaagggat tggggggatcc tatcagccgt     660 tcccagctgg tgaagtccga gctggaggag aagaaatccg agttgaggca caagctgaag     720
tacgtgcccc acgagtacat cgagctgatc gagatcgccc ggaacagcac ccaggaccgt     780
atcctggaga tgaaggtgat ggagttcttc atgaaggtgt acggctacag gggcaagcac     840
ctgggcggct ccaggaagcc cgacggcgcc atctacaccg tgggctcccc catcgactac     900
ggcgtgatcg tggacaccaa ggcctactcc ggcggctaca acctgcccat cggccaggcc     960
gacgaaatgc agaggtacgt ggaggagaac cagaccagga acaagcacat caaccccaac    1020
gagtggtgga aggtgtaccc ctccagcgtg accgagttca agttcctgtt cgtgtccggc    1080
```

| cacttcaagg gcaactacaa ggcccagctg accaggctga accacatcac caactgcaac | 1140 |
| ggcgccgtgc tgtccgtgga ggagctcctg atcggcggcg agatgatcaa ggccggcacc | 1200 |
| ctgaccctgg aggaggtgag gaggaagttc aacaacggcg agatcaactt cgcggccgct | 1260 |

<210> SEQ ID NO 5
<211> LENGTH: 1716
<212> TYPE: DNA
<213> ORGANISM: artificial sequence
<220> FEATURE:
<223> OTHER INFORMATION: synthetic polynucleotide: pCLS8426

<400> SEQUENCE: 5

| atgggcgatc ctaaaaagaa acgtaaggtc atcgattacc catacgatgt tccagattac | 60 |
| gctatcgata tcgccgaccc cattcgttcg cgcacaccaa gtcctgcccg cgagcttctg | 120 |
| cccggacccc aacccgatgg ggttcagccg actgcagatc gtggggtgtc tccgcctgcc | 180 |
| ggcggccccc tggatggctt gccggctcgg cggacgatgt cccggacccg gctgccatct | 240 |
| cccctgccc cctcacctgc gttctcggcg ggcagcttca gtgacctgtt acgtcagttc | 300 |
| gatccgtcac ttttaatac atcgcttttt gattcattgc ctcccttcgg cgctcaccat | 360 |
| acagaggctg ccacaggcga gtgggatgag gtgcaatcgg gtctgcgggc agccgacgcc | 420 |
| cccccaccca ccatgcgcgt ggctgtcact gccgcgcggc cccgcgcgc caagccggcg | 480 |
| ccgcgacgac gtgctgcgca acctccgac gcttcgccgg cggcgcaggt ggatctacgc | 540 |
| acgctcggct acagccagca gcaacaggag aagatcaaac cgaaggttcg ttcgacagtg | 600 |
| gcgcagcacc acgaggcact ggtcggccac gggtttacac acgcgcacat cgttgcgtta | 660 |
| agccaacacc cggcagcgtt agggaccgtc gctgtcaagt atcaggacat gatcgcagcg | 720 |
| ttgccagagg cgacacacga agcgatcgtt ggcgtcggca aacagtggtc cggcgcacgc | 780 |
| gctctggagg ccttgctcac ggtggcggga gagttgagag gtccaccgtt acagttggac | 840 |
| acaggccaac ttctcaagat tgcaaaacgt ggcggcgtga ccgcagtgga ggcagtgcat | 900 |
| gcatggcgca atgcactgac gggtgccccg ctcaacttga ccggagacgc ccgggggatc | 960 |
| aggtcacgtg cgtctcggag cattgttgcc cagttatctc gccctgatcc ggcgttggcc | 1020 |
| gcgttgacca acgaccacct cgtcgccttg gcctgcctcg gcgggcgtcc tgcgctggat | 1080 |
| gcagtgaaaa agggattggg ggatcctatc agccgttccc agctggtgaa gtccgagctg | 1140 |
| gaggagaaga atccgagttg aggcacaag ctgaagtacg tgccccacga gtacatcgag | 1200 |
| ctgatcgaga tcgcccggaa cagcacccag gaccgtatcc tggagatgaa ggtgatggag | 1260 |
| ttcttcatga aggtgtacgg ctacaggggc aagcacctgg gcggctccag gaagcccgac | 1320 |
| ggcgccatct acaccgtggg ctcccccatc gactacggcg tgatcgtgga caccaaggcc | 1380 |
| tactccggcg gctacaacct gcccatcggc caggccgacg aaatgcagag gtacgtggag | 1440 |
| gagaaccaga ccaggaacaa gcacatcaac cccaacgagt ggtggaaggt gtaccctcc | 1500 |
| agcgtgaccg agttcaagtt cctgttcgtg tccggcacct tcaagggcaa ctacaaggcc | 1560 |
| cagctgacca ggctgaacca catcaccaac tgcaacggcg ccgtgctgtc cgtggaggag | 1620 |
| ctcctgatcg gcggcgagat gatcaaggcc ggcaccctga ccctggagga ggtgaggagg | 1680 |
| aagttcaaca acggcgagat caacttcgcg gccgct | 1716 |

<210> SEQ ID NO 6
<211> LENGTH: 2219
<212> TYPE: DNA
<213> ORGANISM: artificial sequence
<220> FEATURE:
<223> OTHER INFORMATION: synthetic polynucleotide: pCLS7183

<400> SEQUENCE: 6

| | | | | | |
|---|---|---|---|---|---|
| ccatggccga | ccccattcgt | tcgcgcacac | caagtcctgc | ccgcgagctt | ctgcccggac | 60 |
| cccaacccga | tggggttcag | ccgactgcag | atcgtggggt | gtctccgcct | gccggcggcc | 120 |
| ccctggatgg | cttgccggct | cggcggacga | tgtcccggac | ccggctgcca | tctcccctg | 180 |
| cccctcacc | tgcgttctcg | gcgggcagct | tcagtgacct | gttacgtcag | ttcgatccgt | 240 |
| cactttttaa | tacatcgctt | tttgattcat | tgcctcccct | cggcgctcac | catacagagg | 300 |
| ctgccacagg | cgagtgggat | gaggtgcaat | cgggtctgcg | ggcagccgac | gccccccac | 360 |
| ccaccatgcg | cgtggctgtc | actgccgcgc | ggccccgcg | cgccaagccg | gcgccgcgac | 420 |
| gacgtgctgc | gcaaccctcc | gacgcttcgc | cggcggcgca | ggtggatcta | cgcacgctcg | 480 |
| gctacagcca | gcagcaacag | gagaagatca | aaccgaaggt | tcgttcgaca | gtggcgcagc | 540 |
| accacgaggc | actggtcggc | cacgggttta | cacgcgcgca | catcgttgcg | ttaagccaac | 600 |
| acccggcagc | gttagggacc | gtcgctgtca | agtatcagga | catgatcgca | gcgttgccag | 660 |
| aggcgacaca | cgaagcgatc | gttggcgtcg | gcaaacagtg | gtccggcgca | cgcgctctgg | 720 |
| aggccttgct | cacggtggcg | ggagagttga | gaggtccacc | gttacagttg | gacacaggcc | 780 |
| aacttctcaa | gattgcaaaa | cgtggcgcg | tgaccgcagt | ggaggcagtg | catgcatggc | 840 |
| gcaatgcact | gacgggtgcc | ccgctcaact | tgaccggaga | cgcccggggg | atcaggtcac | 900 |
| gtgcgtctcg | gagcattgtt | gcccagttat | ctcgccctga | tccggcgttg | gccgcgttga | 960 |
| ccaacgacca | cctcgtcgcc | ttggcctgcc | tcggcgggcg | tcctgcgctg | gatgcagtga | 1020 |
| aaaagggatt | gccgcacgcg | ccggccttga | tcaaaagaac | caatcgccgt | attcccgaac | 1080 |
| gcacatccca | tcgcgttgcc | gaccacgcgc | aagtggttcg | cgtgctgggt | tttttccagt | 1140 |
| gccactccca | cccagcgcaa | gcatttgatg | acgccatgac | gcagttcggg | atgagcaggc | 1200 |
| acgggttgtt | acagctcttt | cgcagagtgg | gcgtcaccga | actcgaagcc | cgcagtggaa | 1260 |
| cgctcccccc | agccagtcag | cgttgggacc | gtatcctcca | ggcatcaggg | atgaaaaggg | 1320 |
| ccaaaccgtc | ccctacttca | actcaaacgc | cggatcaggc | gtctttgcat | gcattcgccg | 1380 |
| attcgctgga | gcgtgacctt | gatgcgccta | gcccaatgca | cgagggagat | cagacgcggg | 1440 |
| caagtagccg | taaacggtcc | cgatcggatc | gtgctgtcac | cggtccctcc | gcacagcaat | 1500 |
| cgttcgaggt | gcgcgttccc | gaacagcgcg | atgcgctcca | tttgcccctc | tcctggaggg | 1560 |
| taaaacgccc | gcgtaccagt | atcggggcg | gcctcccgga | tcctatcagc | cgttcccagc | 1620 |
| tggtgaagtc | cgagctggag | gagaagaaat | ccgagttgag | gcacaagctg | aagtacgtgc | 1680 |
| cccacgagta | catcgagctg | atcgagatcg | cccggaacag | cacccaggac | cgtatcctgg | 1740 |
| agatgaaggt | gatggagttc | ttcatgaagg | tgtacggcta | caggggcaag | cacctgggcg | 1800 |
| gctccaggaa | gcccgacggc | gccatctaca | ccgtgggctc | ccccatcgac | tacggcgtga | 1860 |
| tcgtggacac | caaggcctac | tccggcggct | acaacctgcc | catcggccag | gccgacgaaa | 1920 |
| tgcagaggta | cgtggaggag | aaccagacca | ggaacaagca | catcaacccc | aacgagtggt | 1980 |
| ggaaggtgta | cccctccagc | gtgaccgagt | tcaagttcct | gttcgtgtcc | ggccacttca | 2040 |
| agggcaacta | caaggcccag | ctgaccaggc | tgaaccacat | caccaactgc | aacggcgccg | 2100 |
| tgctgtccgt | ggaggagctc | ctgatcgcg | gcgagatgat | caaggccggc | accctgaccc | 2160 |
| tggaggaggt | gaggaggaag | ttcaacaacg | gcagatcaa | cttcgcggcc | gactgataa | 2219 |

<210> SEQ ID NO 7
<211> LENGTH: 287
<212> TYPE: PRT
<213> ORGANISM: artificial sequence
<220> FEATURE:
<223> OTHER INFORMATION: synthetic polypeptide: complete Nter domain of
     AvrBs3

<400> SEQUENCE: 7

Asp Pro Ile Arg Ser Arg Thr Pro Ser Pro Ala Arg Glu Leu Leu Pro
1               5                   10                  15

Gly Pro Gln Pro Asp Gly Val Gln Pro Thr Ala Asp Arg Gly Val Ser
            20                  25                  30

Pro Pro Ala Gly Gly Pro Leu Asp Gly Leu Pro Ala Arg Arg Thr Met
        35                  40                  45

Ser Arg Thr Arg Leu Pro Ser Pro Pro Ala Pro Ser Pro Ala Phe Ser
    50                  55                  60

Ala Gly Ser Phe Ser Asp Leu Leu Arg Gln Phe Asp Pro Ser Leu Phe
65                  70                  75                  80

Asn Thr Ser Leu Phe Asp Ser Leu Pro Pro Phe Gly Ala His His Thr
                85                  90                  95

Glu Ala Ala Thr Gly Glu Trp Asp Glu Val Gln Ser Gly Leu Arg Ala
            100                 105                 110

Ala Asp Ala Pro Pro Pro Thr Met Arg Val Ala Val Thr Ala Ala Arg
        115                 120                 125

Pro Pro Arg Ala Lys Pro Ala Pro Arg Arg Arg Ala Ala Gln Pro Ser
    130                 135                 140

Asp Ala Ser Pro Ala Ala Gln Val Asp Leu Arg Thr Leu Gly Tyr Ser
145                 150                 155                 160

Gln Gln Gln Gln Glu Lys Ile Lys Pro Lys Val Arg Ser Thr Val Ala
                165                 170                 175

Gln His His Glu Ala Leu Val Gly His Gly Phe Thr His Ala His Ile
            180                 185                 190

Val Ala Leu Ser Gln His Pro Ala Ala Leu Gly Thr Val Ala Val Lys
        195                 200                 205

Tyr Gln Asp Met Ile Ala Ala Leu Pro Glu Ala Thr His Glu Ala Ile
    210                 215                 220

Val Gly Val Gly Lys Gln Trp Ser Gly Ala Arg Ala Leu Glu Ala Leu
225                 230                 235                 240

Leu Thr Val Ala Gly Glu Leu Arg Gly Pro Pro Leu Gln Leu Asp Thr
                245                 250                 255

Gly Gln Leu Leu Lys Ile Ala Lys Arg Gly Gly Val Thr Ala Val Glu
            260                 265                 270

Ala Val His Ala Trp Arg Asn Ala Leu Thr Gly Ala Pro Leu Asn
        275                 280                 285

<210> SEQ ID NO 8
<211> LENGTH: 135
<212> TYPE: PRT
<213> ORGANISM: artificial sequence
<220> FEATURE:
<223> OTHER INFORMATION: synthetic polypeptide: Delta152 Nter domain of
     AvrBs3

-continued

```
<400> SEQUENCE: 8

Asp Leu Arg Thr Leu Gly Tyr Ser Gln Gln Gln Glu Lys Ile Lys
1               5                   10                  15

Pro Lys Val Arg Ser Thr Val Ala Gln His His Glu Ala Leu Val Gly
            20                  25                  30

His Gly Phe Thr His Ala His Ile Val Ala Leu Ser Gln His Pro Ala
        35                  40                  45

Ala Leu Gly Thr Val Ala Val Lys Tyr Gln Asp Met Ile Ala Ala Leu
    50                  55                  60

Pro Glu Ala Thr His Glu Ala Ile Val Gly Val Gly Lys Gln Trp Ser
65                  70                  75                  80

Gly Ala Arg Ala Leu Glu Ala Leu Leu Thr Val Ala Gly Glu Leu Arg
                85                  90                  95

Gly Pro Pro Leu Gln Leu Asp Thr Gly Gln Leu Leu Lys Ile Ala Lys
            100                 105                 110

Arg Gly Gly Val Thr Ala Val Glu Ala Val His Ala Trp Arg Asn Ala
        115                 120                 125

Leu Thr Gly Ala Pro Leu Asn
    130                 135

<210> SEQ ID NO 9
<211> LENGTH: 598
<212> TYPE: PRT
<213> ORGANISM: artificial sequence
<220> FEATURE:
<223> OTHER INFORMATION: synthetic polypeptide: AvrBs3 repeat module

<400> SEQUENCE: 9

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser Asn
65                  70                  75                  80

Ile Gly Gly Lys Gln Ala Leu Glu Thr Val Gln Ala Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser Asn Ile Gly Gly Lys Gln Ala Leu Glu Thr Val Gln Ala
145                 150                 155                 160

Leu Leu Pro Val Leu Cys Gln Ala His Gly Leu Thr Pro Glu Gln Val
                165                 170                 175

Val Ala Ile Ala Ser Asn Ile Gly Gly Lys Gln Ala Leu Glu Thr Val
            180                 185                 190
```

-continued

```
Gln Ala Leu Leu Pro Val Leu Cys Gln Ala His Gly Leu Thr Pro Glu
            195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Glu Gln Val Val Ala Ile Ala
    370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Lys Gln Ala
        515                 520                 525

Leu Glu Thr Val Gln Arg Leu Leu Pro Val Leu Cys Gln Ala His Gly
    530                 535                 540

Leu Thr Pro Glu Gln Val Val Ala Ile Ala Ser His Asp Gly Gly Lys
545                 550                 555                 560

Gln Ala Leu Glu Thr Val Gln Arg Leu Leu Pro Val Leu Cys Gln Ala
                565                 570                 575

His Gly Leu Thr Pro Gln Gln Val Val Ala Ile Ala Ser Asn Gly Gly
            580                 585                 590

Gly Arg Pro Ala Leu Glu
        595
```

-continued

<210> SEQ ID NO 10
<211> LENGTH: 19
<212> TYPE: DNA
<213> ORGANISM: artificial sequence
<220> FEATURE:
<223> OTHER INFORMATION: description of artificial sequence: AvrBs3
      target sequence

<400> SEQUENCE: 10
tatataaacc taaccctct                                              19

<210> SEQ ID NO 11
<211> LENGTH: 1213
<212> TYPE: PRT
<213> ORGANISM: artificial sequence
<220> FEATURE:
<223> OTHER INFORMATION: synthetic polypeptide: pCLS14333

<400> SEQUENCE: 11

Met Gly Asp Pro Lys Lys Lys Arg Lys Val Ile Asp Tyr Pro Tyr Asp
1               5                   10                  15

Val Pro Asp Tyr Ala Ile Asp Ile Gln Leu Val Lys Ser Glu Leu Glu
            20                  25                  30

Glu Lys Lys Ser Glu Leu Arg His Lys Leu Lys Tyr Val Pro His Glu
        35                  40                  45

Tyr Ile Glu Leu Ile Glu Ile Ala Arg Asn Ser Thr Gln Asp Arg Ile
    50                  55                  60

Leu Glu Met Lys Val Met Glu Phe Phe Met Lys Val Tyr Gly Tyr Arg
65                  70                  75                  80

Gly Lys His Leu Gly Gly Ser Arg Lys Pro Asp Gly Ala Ile Tyr Thr
                85                  90                  95

Val Gly Ser Pro Ile Asp Tyr Gly Val Ile Val Asp Thr Lys Ala Tyr
            100                 105                 110

Ser Gly Gly Tyr Asn Leu Pro Ile Gly Gln Ala Asp Glu Met Gln Arg
        115                 120                 125

Tyr Val Glu Glu Asn Gln Thr Arg Asn Lys His Ile Asn Pro Asn Glu
    130                 135                 140

Trp Trp Lys Val Tyr Pro Ser Ser Val Thr Glu Phe Lys Phe Leu Phe
145                 150                 155                 160

Val Ser Gly His Phe Lys Gly Asn Tyr Lys Ala Gln Leu Thr Arg Leu
                165                 170                 175

Asn His Ile Thr Asn Cys Asn Gly Ala Val Leu Ser Val Glu Glu Leu
            180                 185                 190

Leu Ile Gly Gly Glu Met Ile Lys Ala Gly Thr Leu Thr Leu Glu Glu
        195                 200                 205

Val Arg Arg Lys Phe Asn Asn Gly Glu Ile Asn Phe Ala Ser Ser Gly
    210                 215                 220

Gly Ser Gly Ser Thr Ala Gly Phe Ile Ala Asp Leu Arg Thr Leu Gly
225                 230                 235                 240

Tyr Ser Gln Gln Gln Gln Glu Lys Ile Lys Pro Lys Val Arg Ser Thr
                245                 250                 255

Val Ala Gln His His Glu Ala Leu Val Gly His Gly Phe Thr His Ala
            260                 265                 270

His Ile Val Ala Leu Ser Gln His Pro Ala Ala Leu Gly Thr Val Ala
        275                 280                 285

Val Lys Tyr Gln Asp Met Ile Ala Ala Leu Pro Glu Ala Thr His Glu
    290                 295                 300

```
Ala Ile Val Gly Val Gly Lys Gln Trp Ser Gly Arg Ala Leu Glu
305                 310                 315                 320

Ala Leu Leu Thr Val Ala Gly Glu Leu Arg Gly Pro Leu Gln Leu
                325                 330                 335

Asp Thr Gly Gln Leu Leu Lys Ile Ala Lys Arg Gly Gly Val Thr Ala
                340                 345                 350

Val Glu Ala Val His Ala Trp Arg Asn Ala Leu Thr Gly Ala Pro Leu
                355                 360                 365

Asn Leu Thr Pro Glu Gln Val Val Ala Ile Ala Ser His Asp Gly Gly
    370                 375                 380

Lys Gln Ala Leu Glu Thr Val Gln Arg Leu Leu Pro Val Leu Cys Gln
385                 390                 395                 400

Ala His Gly Leu Thr Pro Gln Gln Val Val Ala Ile Ala Ser Asn Gly
                405                 410                 415

Gly Gly Lys Gln Ala Leu Glu Thr Val Gln Arg Leu Leu Pro Val Leu
                420                 425                 430

Cys Gln Ala His Gly Leu Thr Pro Glu Gln Val Val Ala Ile Ala Ser
                435                 440                 445

Asn Ile Gly Gly Lys Gln Ala Leu Glu Thr Val Gln Ala Leu Leu Pro
    450                 455                 460

Val Leu Cys Gln Ala His Gly Leu Thr Pro Gln Gln Val Val Ala Ile
465                 470                 475                 480

Ala Ser Asn Gly Gly Lys Gln Ala Leu Glu Thr Val Gln Arg Leu
                485                 490                 495

Leu Pro Val Leu Cys Gln Ala His Gly Leu Thr Pro Glu Gln Val Val
                500                 505                 510

Ala Ile Ala Ser Asn Ile Gly Gly Lys Gln Ala Leu Glu Thr Val Gln
                515                 520                 525

Ala Leu Leu Pro Val Leu Cys Gln Ala His Gly Leu Thr Pro Glu Gln
                530                 535                 540

Val Val Ala Ile Ala Ser Asn Ile Gly Gly Lys Gln Ala Leu Glu Thr
545                 550                 555                 560

Val Gln Ala Leu Leu Pro Val Leu Cys Gln Ala His Gly Leu Thr Pro
                565                 570                 575

Glu Gln Val Val Ala Ile Ala Ser Asn Ile Gly Gly Lys Gln Ala Leu
                580                 585                 590

Glu Thr Val Gln Ala Leu Leu Pro Val Leu Cys Gln Ala His Gly Leu
                595                 600                 605

Thr Pro Glu Gln Val Val Ala Ile Ala Ser His Asp Gly Gly Lys Gln
    610                 615                 620

Ala Leu Glu Thr Val Gln Arg Leu Leu Pro Val Leu Cys Gln Ala His
625                 630                 635                 640

Gly Leu Thr Pro Glu Gln Val Val Ala Ile Ala Ser His Asp Gly Gly
                645                 650                 655

Lys Gln Ala Leu Glu Thr Val Gln Arg Leu Leu Pro Val Leu Cys Gln
                660                 665                 670

Ala His Gly Leu Thr Pro Gln Gln Val Val Ala Ile Ala Ser Asn Gly
                675                 680                 685

Gly Gly Lys Gln Ala Leu Glu Thr Val Gln Arg Leu Leu Pro Val Leu
                690                 695                 700

Cys Gln Ala His Gly Leu Thr Pro Glu Gln Val Val Ala Ile Ala Ser
705                 710                 715                 720
```

-continued

Asn Ile Gly Gly Lys Gln Ala Leu Glu Thr Val Gln Ala Leu Leu Pro
            725                 730                 735

Val Leu Cys Gln Ala His Gly Leu Thr Pro Glu Gln Val Val Ala Ile
        740                 745                 750

Ala Ser Asn Ile Gly Gly Lys Gln Ala Leu Glu Thr Val Gln Ala Leu
    755                 760                 765

Leu Pro Val Leu Cys Gln Ala His Gly Leu Thr Pro Glu Gln Val Val
770                 775                 780

Ala Ile Ala Ser His Asp Gly Gly Lys Gln Ala Leu Glu Thr Val Gln
785                 790                 795                 800

Arg Leu Leu Pro Val Leu Cys Gln Ala His Gly Leu Thr Pro Glu Gln
                805                 810                 815

Val Val Ala Ile Ala Ser His Asp Gly Gly Lys Gln Ala Leu Glu Thr
            820                 825                 830

Val Gln Arg Leu Leu Pro Val Leu Cys Gln Ala His Gly Leu Thr Pro
        835                 840                 845

Glu Gln Val Val Ala Ile Ala Ser His Asp Gly Gly Lys Gln Ala Leu
    850                 855                 860

Glu Thr Val Gln Arg Leu Leu Pro Val Leu Cys Gln Ala His Gly Leu
865                 870                 875                 880

Thr Pro Gln Gln Val Val Ala Ile Ala Ser Asn Gly Gly Lys Gln
                885                 890                 895

Ala Leu Glu Thr Val Gln Arg Leu Leu Pro Val Leu Cys Gln Ala His
            900                 905                 910

Gly Leu Thr Pro Glu Gln Val Val Ala Ile Ala Ser His Asp Gly Gly
        915                 920                 925

Lys Gln Ala Leu Glu Thr Val Gln Arg Leu Leu Pro Val Leu Cys Gln
    930                 935                 940

Ala His Gly Leu Thr Pro Gln Gln Val Val Ala Ile Ala Ser Asn Gly
945                 950                 955                 960

Gly Gly Arg Pro Ala Leu Glu Ser Ile Val Ala Gln Leu Ser Arg Pro
                965                 970                 975

Asp Pro Ala Leu Ala Ala Leu Thr Asn Asp His Leu Val Ala Leu Ala
            980                 985                 990

Cys Leu Gly Gly Arg Pro Ala Leu Asp Ala Val Lys Lys Gly Leu Gly
        995                 1000                1005

Asp Pro Ile Ser Arg Ser Gln Leu Val Lys Ser Glu Leu Glu Glu
    1010                1015                1020

Lys Lys Ser Glu Leu Arg His Lys Leu Lys Tyr Val Pro His Glu
    1025                1030                1035

Tyr Ile Glu Leu Ile Glu Ile Ala Arg Asn Ser Thr Gln Asp Arg
    1040                1045                1050

Ile Leu Glu Met Lys Val Met Glu Phe Phe Met Lys Val Tyr Gly
    1055                1060                1065

Tyr Arg Gly Lys His Leu Gly Gly Ser Arg Lys Pro Asp Gly Ala
    1070                1075                1080

Ile Tyr Thr Val Gly Ser Pro Ile Asp Tyr Gly Val Ile Val Asp
    1085                1090                1095

Thr Lys Ala Tyr Ser Gly Gly Tyr Asn Leu Pro Ile Gly Gln Ala
    1100                1105                1110

Asp Glu Met Gln Arg Tyr Val Glu Glu Asn Gln Thr Arg Asn Lys
    1115                1120                1125

His Ile Asn Pro Asn Glu Trp Trp Lys Val Tyr Pro Ser Ser Val
    1130                1135                1140

Thr Glu Phe Lys Phe Leu Phe Val Ser Gly His Phe Lys Gly Asn
    1145                1150                1155

Tyr Lys Ala Gln Leu Thr Arg Leu Asn His Ile Thr Asn Cys Asn
    1160                1165                1170

Gly Ala Val Leu Ser Val Glu Glu Leu Ile Gly Gly Glu Met
    1175                1180                1185

Ile Lys Ala Gly Thr Leu Thr Leu Glu Glu Val Arg Arg Lys Phe
    1190                1195                1200

Asn Asn Gly Glu Ile Asn Phe Ala Ala Asp
    1205                1210

<210> SEQ ID NO 12
<211> LENGTH: 1365
<212> TYPE: PRT
<213> ORGANISM: artificial sequence
<220> FEATURE:
<223> OTHER INFORMATION: synthetic polypeptide: pCLS14944

<400> SEQUENCE: 12

Met Gly Asp Pro Lys Lys Arg Lys Val Ile Asp Tyr Pro Tyr Asp
1               5                   10                  15

Val Pro Asp Tyr Ala Ile Asp Ile Gln Leu Val Lys Ser Glu Leu Glu
            20                  25                  30

Glu Lys Lys Ser Glu Leu Arg His Lys Leu Lys Tyr Val Pro His Glu
        35                  40                  45

Tyr Ile Glu Leu Ile Glu Ile Ala Arg Asn Ser Thr Gln Asp Arg Ile
    50                  55                  60

Leu Glu Met Lys Val Met Glu Phe Phe Met Lys Val Tyr Gly Tyr Arg
65                  70                  75                  80

Gly Lys His Leu Gly Gly Ser Arg Lys Pro Asp Gly Ala Ile Tyr Thr
            85                  90                  95

Val Gly Ser Pro Ile Asp Tyr Gly Val Ile Val Asp Thr Lys Ala Tyr
            100                 105                 110

Ser Gly Gly Tyr Asn Leu Pro Ile Gly Gln Ala Asp Glu Met Gln Arg
        115                 120                 125

Tyr Val Glu Glu Asn Gln Thr Arg Asn Lys His Ile Asn Pro Asn Glu
    130                 135                 140

Trp Trp Lys Val Tyr Pro Ser Ser Val Thr Glu Phe Lys Phe Leu Phe
145                 150                 155                 160

Val Ser Gly His Phe Lys Gly Asn Tyr Lys Ala Gln Leu Thr Arg Leu
            165                 170                 175

Asn His Ile Thr Asn Cys Asn Gly Ala Val Leu Ser Val Glu Glu Leu
            180                 185                 190

Leu Ile Gly Gly Glu Met Ile Lys Ala Gly Thr Leu Thr Leu Glu Glu
        195                 200                 205

Val Arg Arg Lys Phe Asn Asn Gly Glu Ile Asn Phe Ala Ser Ser Gly
    210                 215                 220

Gly Ser Gly Ser Thr Ala Gly Phe Ile Ala Asp Pro Ile Arg Ser Arg
225                 230                 235                 240

Thr Pro Ser Pro Ala Arg Glu Leu Leu Pro Gly Pro Gln Pro Asp Gly
            245                 250                 255

Val Gln Pro Thr Ala Asp Arg Gly Val Ser Pro Pro Ala Gly Gly Pro
            260                 265                 270

```
Leu Asp Gly Leu Pro Ala Arg Arg Thr Met Ser Arg Thr Arg Leu Pro
            275                 280                 285

Ser Pro Pro Ala Pro Ser Pro Ala Phe Ser Ala Gly Ser Phe Ser Asp
290                 295                 300

Leu Leu Arg Gln Phe Asp Pro Ser Leu Phe Asn Thr Ser Leu Phe Asp
305                 310                 315                 320

Ser Leu Pro Pro Phe Gly Ala His His Thr Glu Ala Ala Thr Gly Glu
                325                 330                 335

Trp Asp Glu Val Gln Ser Gly Leu Arg Ala Ala Asp Ala Pro Pro
                340                 345                 350

Thr Met Arg Val Ala Val Thr Ala Ala Arg Pro Pro Arg Ala Lys Pro
            355                 360                 365

Ala Pro Arg Arg Arg Ala Ala Gln Pro Ser Asp Ala Ser Pro Ala Ala
370                 375                 380

Gln Val Asp Leu Arg Thr Leu Gly Tyr Ser Gln Gln Gln Gln Glu Lys
385                 390                 395                 400

Ile Lys Pro Lys Val Arg Ser Thr Val Ala Gln His His Glu Ala Leu
                405                 410                 415

Val Gly His Gly Phe Thr His Ala His Ile Val Ala Leu Ser Gln His
                420                 425                 430

Pro Ala Ala Leu Gly Thr Val Ala Val Lys Tyr Gln Asp Met Ile Ala
            435                 440                 445

Ala Leu Pro Glu Ala Thr His Glu Ala Ile Val Gly Val Gly Lys Gln
            450                 455                 460

Trp Ser Gly Ala Arg Ala Leu Glu Ala Leu Leu Thr Val Ala Gly Glu
465                 470                 475                 480

Leu Arg Gly Pro Pro Leu Gln Leu Asp Thr Gly Gln Leu Leu Lys Ile
                485                 490                 495

Ala Lys Arg Gly Gly Val Thr Ala Val Glu Ala Val His Ala Trp Arg
            500                 505                 510

Asn Ala Leu Thr Gly Ala Pro Leu Asn Leu Thr Pro Glu Gln Val Val
            515                 520                 525

Ala Ile Ala Ser His Asp Gly Gly Lys Gln Ala Leu Glu Thr Val Gln
            530                 535                 540

Arg Leu Leu Pro Val Leu Cys Gln Ala His Gly Leu Thr Pro Gln Gln
545                 550                 555                 560

Val Val Ala Ile Ala Ser Asn Gly Gly Lys Gln Ala Leu Glu Thr
                565                 570                 575

Val Gln Arg Leu Leu Pro Val Leu Cys Gln Ala His Gly Leu Thr Pro
            580                 585                 590

Glu Gln Val Val Ala Ile Ala Ser Asn Ile Gly Gly Lys Gln Ala Leu
                595                 600                 605

Glu Thr Val Gln Ala Leu Leu Pro Val Leu Cys Gln Ala His Gly Leu
            610                 615                 620

Thr Pro Gln Gln Val Val Ala Ile Ala Ser Asn Gly Gly Gly Lys Gln
625                 630                 635                 640

Ala Leu Glu Thr Val Gln Arg Leu Leu Pro Val Leu Cys Gln Ala His
                645                 650                 655

Gly Leu Thr Pro Glu Gln Val Val Ala Ile Ala Ser Asn Ile Gly Gly
                660                 665                 670

Lys Gln Ala Leu Glu Thr Val Gln Ala Leu Leu Pro Val Leu Cys Gln
                675                 680                 685
```

```
Ala His Gly Leu Thr Pro Glu Gln Val Val Ala Ile Ala Ser Asn Ile
    690             695                 700
Gly Gly Lys Gln Ala Leu Glu Thr Val Gln Ala Leu Leu Pro Val Leu
705                 710                 715                 720
Cys Gln Ala His Gly Leu Thr Pro Glu Gln Val Val Ala Ile Ala Ser
                725                 730                 735
Asn Ile Gly Gly Lys Gln Ala Leu Glu Thr Val Gln Ala Leu Leu Pro
            740                 745                 750
Val Leu Cys Gln Ala His Gly Leu Thr Pro Glu Gln Val Val Ala Ile
        755                 760                 765
Ala Ser His Asp Gly Gly Lys Gln Ala Leu Glu Thr Val Gln Arg Leu
770                 775                 780
Leu Pro Val Leu Cys Gln Ala His Gly Leu Thr Pro Glu Gln Val Val
785                 790                 795                 800
Ala Ile Ala Ser His Asp Gly Gly Lys Gln Ala Leu Glu Thr Val Gln
                805                 810                 815
Arg Leu Leu Pro Val Leu Cys Gln Ala His Gly Leu Thr Pro Gln Gln
            820                 825                 830
Val Val Ala Ile Ala Ser Asn Gly Gly Lys Gln Ala Leu Glu Thr
        835                 840                 845
Val Gln Arg Leu Leu Pro Val Leu Cys Gln Ala His Gly Leu Thr Pro
850                 855                 860
Glu Gln Val Val Ala Ile Ala Ser Asn Ile Gly Gly Lys Gln Ala Leu
865                 870                 875                 880
Glu Thr Val Gln Ala Leu Leu Pro Val Leu Cys Gln Ala His Gly Leu
                885                 890                 895
Thr Pro Glu Gln Val Val Ala Ile Ala Ser Asn Ile Gly Gly Lys Gln
            900                 905                 910
Ala Leu Glu Thr Val Gln Ala Leu Leu Pro Val Leu Cys Gln Ala His
        915                 920                 925
Gly Leu Thr Pro Glu Gln Val Val Ala Ile Ala Ser His Asp Gly Gly
930                 935                 940
Lys Gln Ala Leu Glu Thr Val Gln Arg Leu Leu Pro Val Leu Cys Gln
945                 950                 955                 960
Ala His Gly Leu Thr Pro Glu Gln Val Val Ala Ile Ala Ser His Asp
                965                 970                 975
Gly Gly Lys Gln Ala Leu Glu Thr Val Gln Arg Leu Leu Pro Val Leu
            980                 985                 990
Cys Gln Ala His Gly Leu Thr Pro Glu Gln Val Val Ala Ile Ala Ser
        995                 1000                1005
His Asp Gly Gly Lys Gln Ala Leu Glu Thr Val Gln Arg Leu Leu
    1010            1015                1020
Pro Val Leu Cys Gln Ala His Gly Leu Thr Pro Gln Gln Val Val
    1025            1030                1035
Ala Ile Ala Ser Asn Gly Gly Lys Gln Ala Leu Glu Thr Val
    1040            1045                1050
Gln Arg Leu Leu Pro Val Leu Cys Gln Ala His Gly Leu Thr Pro
    1055            1060                1065
Glu Gln Val Val Ala Ile Ala Ser His Asp Gly Gly Lys Gln Ala
    1070            1075                1080
Leu Glu Thr Val Gln Arg Leu Leu Pro Val Leu Cys Gln Ala His
    1085            1090                1095
```

```
Gly Leu Thr Pro Gln Gln Val Val Ala Ile Ala Ser Asn Gly Gly
    1100                1105                1110

Gly Arg Pro Ala Leu Glu Ser Ile Val Ala Gln Leu Ser Arg Pro
    1115                1120                1125

Asp Pro Ala Leu Ala Ala Leu Thr Asn Asp His Leu Val Ala Leu
    1130                1135                1140

Ala Cys Leu Gly Gly Arg Pro Ala Leu Asp Ala Val Lys Lys Gly
    1145                1150                1155

Leu Gly Asp Pro Ile Ser Arg Ser Gln Leu Val Lys Ser Glu Leu
    1160                1165                1170

Glu Glu Lys Lys Ser Glu Leu Arg His Lys Leu Lys Tyr Val Pro
    1175                1180                1185

His Glu Tyr Ile Glu Leu Ile Glu Ile Ala Arg Asn Ser Thr Gln
    1190                1195                1200

Asp Arg Ile Leu Glu Met Lys Val Met Glu Phe Phe Met Lys Val
    1205                1210                1215

Tyr Gly Tyr Arg Gly Lys His Leu Gly Gly Ser Arg Lys Pro Asp
    1220                1225                1230

Gly Ala Ile Tyr Thr Val Gly Ser Pro Ile Asp Tyr Gly Val Ile
    1235                1240                1245

Val Asp Thr Lys Ala Tyr Ser Gly Gly Tyr Asn Leu Pro Ile Gly
    1250                1255                1260

Gln Ala Asp Glu Met Gln Arg Tyr Val Glu Glu Asn Gln Thr Arg
    1265                1270                1275

Asn Lys His Ile Asn Pro Asn Glu Trp Trp Lys Val Tyr Pro Ser
    1280                1285                1290

Ser Val Thr Glu Phe Lys Phe Leu Phe Val Ser Gly His Phe Lys
    1295                1300                1305

Gly Asn Tyr Lys Ala Gln Leu Thr Arg Leu Asn His Ile Thr Asn
    1310                1315                1320

Cys Asn Gly Ala Val Leu Ser Val Glu Glu Leu Leu Ile Gly Gly
    1325                1330                1335

Glu Met Ile Lys Ala Gly Thr Leu Thr Leu Glu Glu Val Arg Arg
    1340                1345                1350

Lys Phe Asn Asn Gly Glu Ile Asn Phe Ala Ala Asp
    1355                1360                1365

<210> SEQ ID NO 13
<211> LENGTH: 530
<212> TYPE: PRT
<213> ORGANISM: artificial sequence
<220> FEATURE:
<223> OTHER INFORMATION: description of artificial sequence: synthetic
      polypeptide

<400> SEQUENCE: 13

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Glu Gln Val Val Ala Ile Ala Ser His Asp Gly
            35                  40                  45

Gly Lys Gln Ala Leu Glu Thr Val Gln Arg Leu Leu Pro Val Leu Cys
        50                  55                  60

Gln Ala His Gly Leu Thr Pro Gln Gln Val Val Ala Ile Ala Ser Asn
65                  70                  75                  80
```

```
Gly Gly Gly Lys Gln Ala Leu Glu Thr Val Gln Arg Leu Leu Pro Val
                85                  90                  95
Leu Cys Gln Ala His Gly Leu Thr Pro Gln Gln Val Val Ala Ile Ala
            100                 105                 110
Ser Asn Asn Gly Gly Lys Gln Ala Leu Glu Thr Val Gln Arg Leu Leu
            115                 120                 125
Pro Val Leu Cys Gln Ala His Gly Leu Thr Pro Glu Gln Val Val Ala
        130                 135                 140
Ile Ala Ser His Asp Gly Gly Lys Gln Ala Leu Glu Thr Val Gln Arg
145                 150                 155                 160
Leu Leu Pro Val Leu Cys Gln Ala His Gly Leu Thr Pro Gln Gln Val
                165                 170                 175
Val Ala Ile Ala Ser Asn Gly Gly Lys Gln Ala Leu Glu Thr Val
            180                 185                 190
Gln Arg Leu Leu Pro Val Leu Cys Gln Ala His Gly Leu Thr Pro Gln
        195                 200                 205
Gln Val Val Ala Ile Ala Ser Asn Asn Gly Gly Lys Gln Ala Leu Glu
    210                 215                 220
Thr Val Gln Arg Leu Leu Pro Val Leu Cys Gln Ala His Gly Leu Thr
225                 230                 235                 240
Pro Glu Gln Val Val Ala Ile Ala Ser His Asp Gly Gly Lys Gln Ala
                245                 250                 255
Leu Glu Thr Val Gln Arg Leu Leu Pro Val Leu Cys Gln Ala His Gly
            260                 265                 270
Leu Thr Pro Gln Gln Val Val Ala Ile Ala Ser Asn Gly Gly Gly Lys
        275                 280                 285
Gln Ala Leu Glu Thr Val Gln Arg Leu Leu Pro Val Leu Cys Gln Ala
    290                 295                 300
His Gly Leu Thr Pro Gln Gln Val Val Ala Ile Ala Ser Asn Asn Gly
305                 310                 315                 320
Gly Lys Gln Ala Leu Glu Thr Val Gln Arg Leu Leu Pro Val Leu Cys
                325                 330                 335
Gln Ala His Gly Leu Thr Pro Glu Gln Val Val Ala Ile Ala Ser His
            340                 345                 350
Asp Gly Gly Lys Gln Ala Leu Glu Thr Val Gln Arg Leu Leu Pro Val
        355                 360                 365
Leu Cys Gln Ala His Gly Leu Thr Pro Gln Gln Val Val Ala Ile Ala
    370                 375                 380
Ser Asn Gly Gly Lys Gln Ala Leu Glu Thr Val Gln Arg Leu Leu
385                 390                 395                 400
Pro Val Leu Cys Gln Ala His Gly Leu Thr Pro Gln Gln Val Val Ala
                405                 410                 415
Ile Ala Ser Asn Asn Gly Gly Lys Gln Ala Leu Glu Thr Val Gln Arg
            420                 425                 430
Leu Leu Pro Val Leu Cys Gln Ala His Gly Leu Thr Pro Glu Gln Val
        435                 440                 445
Val Ala Ile Ala Ser His Asp Gly Gly Lys Gln Ala Leu Glu Thr Val
    450                 455                 460
Gln Arg Leu Leu Pro Val Leu Cys Gln Ala His Gly Leu Thr Pro Gln
465                 470                 475                 480
Gln Val Val Ala Ile Ala Ser Asn Gly Gly Gly Lys Gln Ala Leu Glu
                485                 490                 495
```

```
Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 14
<211> LENGTH: 16
<212> TYPE: DNA
<213> ORGANISM: artificial sequence
<220> FEATURE:
<223> OTHER INFORMATION: description of artificial sequence: target
      sequence

<400> SEQUENCE: 14
gctgctgctg ctgctg                                                        16

<210> SEQ ID NO 15
<211> LENGTH: 1145
<212> TYPE: PRT
<213> ORGANISM: artificial sequence
<220> FEATURE:
<223> OTHER INFORMATION: synthetic polypeptide: pCLS14332

<400> SEQUENCE: 15

Met Gly Asp Pro Lys Lys Arg Lys Val Ile Asp Tyr Pro Tyr Asp
1               5                   10                  15

Val Pro Asp Tyr Ala Ile Asp Ile Gln Leu Val Lys Ser Glu Leu Glu
            20                  25                  30

Glu Lys Lys Ser Glu Leu Arg His Lys Leu Lys Tyr Val Pro His Glu
        35                  40                  45

Tyr Ile Glu Leu Ile Glu Ile Ala Arg Asn Ser Thr Gln Asp Arg Ile
    50                  55                  60

Leu Glu Met Lys Val Met Glu Phe Phe Met Lys Val Tyr Gly Tyr Arg
65                  70                  75                  80

Gly Lys His Leu Gly Gly Ser Arg Lys Pro Asp Gly Ala Ile Tyr Thr
                85                  90                  95

Val Gly Ser Pro Ile Asp Tyr Gly Val Ile Val Asp Thr Lys Ala Tyr
            100                 105                 110

Ser Gly Gly Tyr Asn Leu Pro Ile Gly Gln Ala Asp Glu Met Gln Arg
        115                 120                 125

Tyr Val Glu Glu Asn Gln Thr Arg Asn Lys His Ile Asn Pro Asn Glu
    130                 135                 140

Trp Trp Lys Val Tyr Pro Ser Ser Val Thr Glu Phe Lys Phe Leu Phe
145                 150                 155                 160

Val Ser Gly His Phe Lys Gly Asn Tyr Lys Ala Gln Leu Thr Arg Leu
                165                 170                 175

Asn His Ile Thr Asn Cys Asn Gly Ala Val Leu Ser Val Glu Glu Leu
            180                 185                 190

Leu Ile Gly Gly Glu Met Ile Lys Ala Gly Thr Leu Thr Leu Glu Glu
        195                 200                 205

Val Arg Arg Lys Phe Asn Asn Gly Glu Ile Asn Phe Ala Ser Ser Gly
    210                 215                 220

Gly Ser Gly Ser Thr Ala Gly Phe Ile Ala Asp Leu Arg Thr Leu Gly
225                 230                 235                 240

Tyr Ser Gln Gln Gln Gln Glu Lys Ile Lys Pro Lys Val Arg Ser Thr
                245                 250                 255
```

```
Val Ala Gln His His Glu Ala Leu Val Gly His Gly Phe Thr His Ala
            260                 265                 270

His Ile Val Ala Leu Ser Gln His Pro Ala Ala Leu Gly Thr Val Ala
            275                 280                 285

Val Lys Tyr Gln Asp Met Ile Ala Ala Leu Pro Glu Ala Thr His Glu
            290                 295                 300

Ala Ile Val Gly Val Gly Lys Gln Trp Ser Gly Ala Arg Ala Leu Glu
305                 310                 315                 320

Ala Leu Leu Thr Val Ala Gly Glu Leu Arg Gly Pro Pro Leu Gln Leu
                325                 330                 335

Asp Thr Gly Gln Leu Leu Lys Ile Ala Lys Arg Gly Gly Val Thr Ala
            340                 345                 350

Val Glu Ala Val His Ala Trp Arg Asn Ala Leu Thr Gly Ala Pro Leu
            355                 360                 365

Asn Leu Thr Pro Gln Gln Val Val Ala Ile Ala Ser Asn Asn Gly Gly
            370                 375                 380

Lys Gln Ala Leu Glu Thr Val Gln Arg Leu Leu Pro Val Leu Cys Gln
385                 390                 395                 400

Ala His Gly Leu Thr Pro Glu Gln Val Val Ala Ile Ala Ser His Asp
            405                 410                 415

Gly Gly Lys Gln Ala Leu Glu Thr Val Gln Arg Leu Leu Pro Val Leu
            420                 425                 430

Cys Gln Ala His Gly Leu Thr Pro Gln Gln Val Val Ala Ile Ala Ser
            435                 440                 445

Asn Gly Gly Gly Lys Gln Ala Leu Glu Thr Val Gln Arg Leu Leu Pro
450                 455                 460

Val Leu Cys Gln Ala His Gly Leu Thr Pro Gln Gln Val Val Ala Ile
465                 470                 475                 480

Ala Ser Asn Asn Gly Gly Lys Gln Ala Leu Glu Thr Val Gln Arg Leu
            485                 490                 495

Leu Pro Val Leu Cys Gln Ala His Gly Leu Thr Pro Glu Gln Val Val
            500                 505                 510

Ala Ile Ala Ser His Asp Gly Gly Lys Gln Ala Leu Glu Thr Val Gln
            515                 520                 525

Arg Leu Leu Pro Val Leu Cys Gln Ala His Gly Leu Thr Pro Gln Gln
            530                 535                 540

Val Val Ala Ile Ala Ser Asn Gly Gly Gly Lys Gln Ala Leu Glu Thr
545                 550                 555                 560

Val Gln Arg Leu Leu Pro Val Leu Cys Gln Ala His Gly Leu Thr Pro
            565                 570                 575

Gln Gln Val Val Ala Ile Ala Ser Asn Asn Gly Gly Lys Gln Ala Leu
            580                 585                 590

Glu Thr Val Gln Arg Leu Leu Pro Val Leu Cys Gln Ala His Gly Leu
            595                 600                 605

Thr Pro Glu Gln Val Val Ala Ile Ala Ser His Asp Gly Gly Lys Gln
            610                 615                 620

Ala Leu Glu Thr Val Gln Arg Leu Leu Pro Val Leu Cys Gln Ala His
625                 630                 635                 640

Gly Leu Thr Pro Gln Gln Val Val Ala Ile Ala Ser Asn Gly Gly Gly
            645                 650                 655

Lys Gln Ala Leu Glu Thr Val Gln Arg Leu Leu Pro Val Leu Cys Gln
            660                 665                 670
```

Ala His Gly Leu Thr Pro Gln Gln Val Val Ala Ile Ala Ser Asn Asn
            675                 680                 685

Gly Gly Lys Gln Ala Leu Glu Thr Val Gln Arg Leu Leu Pro Val Leu
        690                 695                 700

Cys Gln Ala His Gly Leu Thr Pro Glu Gln Val Val Ala Ile Ala Ser
705                 710                 715                 720

His Asp Gly Gly Lys Gln Ala Leu Glu Thr Val Gln Arg Leu Leu Pro
                725                 730                 735

Val Leu Cys Gln Ala His Gly Leu Thr Pro Gln Gln Val Val Ala Ile
            740                 745                 750

Ala Ser Asn Gly Gly Gly Lys Gln Ala Leu Glu Thr Val Gln Arg Leu
        755                 760                 765

Leu Pro Val Leu Cys Gln Ala His Gly Leu Thr Pro Gln Gln Val Val
770                 775                 780

Ala Ile Ala Ser Asn Asn Gly Gly Lys Gln Ala Leu Glu Thr Val Gln
785                 790                 795                 800

Arg Leu Leu Pro Val Leu Cys Gln Ala His Gly Leu Thr Pro Glu Gln
            805                 810                 815

Val Val Ala Ile Ala Ser His Asp Gly Gly Lys Gln Ala Leu Glu Thr
        820                 825                 830

Val Gln Arg Leu Leu Pro Val Leu Cys Gln Ala His Gly Leu Thr Pro
835                 840                 845

Gln Gln Val Val Ala Ile Ala Ser Asn Gly Gly Gly Lys Gln Ala Leu
850                 855                 860

Glu Thr Val Gln Arg Leu Leu Pro Val Leu Cys Gln Ala His Gly Leu
865                 870                 875                 880

Thr Pro Gln Gln Val Val Ala Ile Ala Ser Asn Gly Gly Gly Arg Pro
                885                 890                 895

Ala Leu Glu Ser Ile Val Ala Gln Leu Ser Arg Pro Asp Pro Ala Leu
            900                 905                 910

Ala Ala Leu Thr Asn Asp His Leu Val Ala Leu Ala Cys Leu Gly Gly
        915                 920                 925

Arg Pro Ala Leu Asp Ala Val Lys Lys Gly Leu Gly Asp Pro Ile Ser
930                 935                 940

Arg Ser Gln Leu Val Lys Ser Glu Leu Glu Glu Lys Ser Glu Leu
945                 950                 955                 960

Arg His Lys Leu Lys Tyr Val Pro His Glu Tyr Ile Glu Leu Ile Glu
            965                 970                 975

Ile Ala Arg Asn Ser Thr Gln Asp Arg Ile Leu Glu Met Lys Val Met
        980                 985                 990

Glu Phe Phe Met Lys Val Tyr Gly Tyr Arg Gly Lys His Leu Gly Gly
        995                 1000                1005

Ser Arg Lys Pro Asp Gly Ala Ile Tyr Thr Val Gly Ser Pro Ile
    1010                1015                1020

Asp Tyr Gly Val Ile Val Asp Thr Lys Ala Tyr Ser Gly Gly Tyr
    1025                1030                1035

Asn Leu Pro Ile Gly Gln Ala Asp Glu Met Gln Arg Tyr Val Glu
    1040                1045                1050

Glu Asn Gln Thr Arg Asn Lys His Ile Asn Pro Asn Glu Trp Trp
    1055                1060                1065

Lys Val Tyr Pro Ser Ser Val Thr Glu Phe Lys Phe Leu Phe Val
    1070                1075                1080

```
Ser Gly His Phe Lys Gly Asn Tyr Lys Ala Gln Leu Thr Arg Leu
    1085                1090                1095

Asn His Ile Thr Asn Cys Asn Gly Ala Val Leu Ser Val Glu Glu
    1100                1105                1110

Leu Leu Ile Gly Gly Glu Met Ile Lys Ala Gly Thr Leu Thr Leu
    1115                1120                1125

Glu Glu Val Arg Arg Lys Phe Asn Asn Gly Glu Ile Asn Phe Ala
    1130                1135                1140

Ala Asp
    1145

<210> SEQ ID NO 16
<211> LENGTH: 43
<212> TYPE: DNA
<213> ORGANISM: artificial sequence
<220> FEATURE:
<223> OTHER INFORMATION: description of artificial sequence: target
      sequence

<400> SEQUENCE: 16
tatataaacc taaccctcta ggtaagaggg ttaggtttat ata            43

<210> SEQ ID NO 17
<211> LENGTH: 44
<212> TYPE: DNA
<213> ORGANISM: artificial sequence
<220> FEATURE:
<223> OTHER INFORMATION: description of artificial sequence: target
      sequence

<400> SEQUENCE: 17
tatataaacc taaccctcta aggtaagagg gttaggttta tata           44

<210> SEQ ID NO 18
<211> LENGTH: 45
<212> TYPE: DNA
<213> ORGANISM: artificial sequence
<220> FEATURE:
<223> OTHER INFORMATION: description of artificial sequence: target
      sequence

<400> SEQUENCE: 18
tatataaacc taaccctcta aggtacagag ggttaggttt atata          45

<210> SEQ ID NO 19
<211> LENGTH: 46
<212> TYPE: DNA
<213> ORGANISM: artificial sequence
<220> FEATURE:
<223> OTHER INFORMATION: description of artificial sequence: target
      sequence

<400> SEQUENCE: 19
tatataaacc taaccctctg aaggtacaga gggttaggtt tatata         46

<210> SEQ ID NO 20
<211> LENGTH: 47
<212> TYPE: DNA
<213> ORGANISM: artificial sequence
<220> FEATURE:
<223> OTHER INFORMATION: description of artificial sequence: target
      sequence

<400> SEQUENCE: 20
tatataaacc taaccctctg aaggtaccag agggttaggt ttatata        47
```

```
<210> SEQ ID NO 21
<211> LENGTH: 48
<212> TYPE: DNA
<213> ORGANISM: artificial sequence
<220> FEATURE:
<223> OTHER INFORMATION: description of artificial sequence: target
      sequence

<400> SEQUENCE: 21
tatataaacc taaccctctt gaaggtacca gagggttagg tttatata                48

<210> SEQ ID NO 22
<211> LENGTH: 49
<212> TYPE: DNA
<213> ORGANISM: artificial sequence
<220> FEATURE:
<223> OTHER INFORMATION: description of artificial sequence: target
      sequence

<400> SEQUENCE: 22
tatataaacc taaccctctt gaaggtacct agagggttag gtttatata               49

<210> SEQ ID NO 23
<211> LENGTH: 50
<212> TYPE: DNA
<213> ORGANISM: artificial sequence
<220> FEATURE:
<223> OTHER INFORMATION: description of artificial sequence: target
      sequence

<400> SEQUENCE: 23
tatataaacc taaccctcta tgaaggtacc tagagggtta ggtttatata              50

<210> SEQ ID NO 24
<211> LENGTH: 51
<212> TYPE: DNA
<213> ORGANISM: artificial sequence
<220> FEATURE:
<223> OTHER INFORMATION: description of artificial sequence: target
      sequence

<400> SEQUENCE: 24
tatataaacc taaccctcta tgaaggtacc ttagagggtt aggtttatat a            51

<210> SEQ ID NO 25
<211> LENGTH: 52
<212> TYPE: DNA
<213> ORGANISM: artificial sequence
<220> FEATURE:
<223> OTHER INFORMATION: description of artificial sequence: target
      sequence

<400> SEQUENCE: 25
tatataaacc taaccctctc atgaaggtac cttagagggt taggtttata ta           52

<210> SEQ ID NO 26
<211> LENGTH: 53
<212> TYPE: DNA
<213> ORGANISM: artificial sequence
<220> FEATURE:
<223> OTHER INFORMATION: description of artificial sequence: target
      sequence

<400> SEQUENCE: 26
tatataaacc taaccctctt agcatgaagg taccagaggg ttaggtttat ata          53
```

```
<210> SEQ ID NO 27
<211> LENGTH: 54
<212> TYPE: DNA
<213> ORGANISM: artificial sequence
<220> FEATURE:
<223> OTHER INFORMATION: description of artificial sequence: target
      sequence

<400> SEQUENCE: 27
tatataaacc taaccctctg catgaaggta ccttgagagg gttaggttta tata            54

<210> SEQ ID NO 28
<211> LENGTH: 55
<212> TYPE: DNA
<213> ORGANISM: artificial sequence
<220> FEATURE:
<223> OTHER INFORMATION: description of artificial sequence: target
      sequence

<400> SEQUENCE: 28
tatataaacc taaccctctg catgaaggta ccttgtagag ggttaggttt atata           55

<210> SEQ ID NO 29
<211> LENGTH: 56
<212> TYPE: DNA
<213> ORGANISM: artificial sequence
<220> FEATURE:
<223> OTHER INFORMATION: description of artificial sequence: target
      sequence

<400> SEQUENCE: 29
tatataaacc taaccctcta gcatgaaggt accttgtaga gggttaggtt tatata          56

<210> SEQ ID NO 30
<211> LENGTH: 57
<212> TYPE: DNA
<213> ORGANISM: artificial sequence
<220> FEATURE:
<223> OTHER INFORMATION: description of artificial sequence: target
      sequence

<400> SEQUENCE: 30
tatataaacc taaccctcta gcatgaaggt accttgtcag agggttaggt ttatata         57

<210> SEQ ID NO 31
<211> LENGTH: 58
<212> TYPE: DNA
<213> ORGANISM: artificial sequence
<220> FEATURE:
<223> OTHER INFORMATION: description of artificial sequence: target
      sequence

<400> SEQUENCE: 31
tatataaacc taaccctctt agcatgaagg taccttgtca gagggttagg tttatata        58

<210> SEQ ID NO 32
<211> LENGTH: 59
<212> TYPE: DNA
<213> ORGANISM: artificial sequence
<220> FEATURE:
<223> OTHER INFORMATION: description of artificial sequence: target
      sequence

<400> SEQUENCE: 32
tatataaacc taaccctctt agcatgaagg taccttgtcg agagggttag gtttatata       59
```

-continued

```
<210> SEQ ID NO 33
<211> LENGTH: 60
<212> TYPE: DNA
<213> ORGANISM: artificial sequence
<220> FEATURE:
<223> OTHER INFORMATION: description of artificial sequence: target
      sequence

<400> SEQUENCE: 33
tatataaacc taaccctctt agcatgaagg taccttgtcg tagagggtta ggtttatata      60

<210> SEQ ID NO 34
<211> LENGTH: 61
<212> TYPE: DNA
<213> ORGANISM: artificial sequence
<220> FEATURE:
<223> OTHER INFORMATION: description of artificial sequence: target
      sequence

<400> SEQUENCE: 34
tatataaacc taaccctctc tagcatgaag gtaccttgtc gtagagggtt aggtttatat      60
a                                                                    61

<210> SEQ ID NO 35
<211> LENGTH: 62
<212> TYPE: DNA
<213> ORGANISM: artificial sequence
<220> FEATURE:
<223> OTHER INFORMATION: description of artificial sequence: target
      sequence

<400> SEQUENCE: 35
tatataaacc taaccctctc tagcatgaag gtaccttgtc gttagagggt taggtttata      60
ta                                                                   62

<210> SEQ ID NO 36
<211> LENGTH: 63
<212> TYPE: DNA
<213> ORGANISM: artificial sequence
<220> FEATURE:
<223> OTHER INFORMATION: description of artificial sequence: target
      sequence

<400> SEQUENCE: 36
tatataaacc taaccctcta ctagcatgaa ggtaccttgt cgttagaggg ttaggtttat      60
ata                                                                  63

<210> SEQ ID NO 37
<211> LENGTH: 64
<212> TYPE: DNA
<213> ORGANISM: artificial sequence
<220> FEATURE:
<223> OTHER INFORMATION: description of artificial sequence: target
      sequence

<400> SEQUENCE: 37
tatataaacc taaccctcta ctagcatgaa ggtaccttgt cgttgagagg gttaggttta      60
tata                                                                 64

<210> SEQ ID NO 38
<211> LENGTH: 65
<212> TYPE: DNA
<213> ORGANISM: artificial sequence
```

```
<220> FEATURE:
<223> OTHER INFORMATION: description of artificial sequence: target
      sequence

<400> SEQUENCE: 38
tatataaacc taaccctctc actagcatga aggtaccttg tcgttgagag ggttaggttt    60
atata                                                                65

<210> SEQ ID NO 39
<211> LENGTH: 66
<212> TYPE: DNA
<213> ORGANISM: artificial sequence
<220> FEATURE:
<223> OTHER INFORMATION: description of artificial sequence: target
      sequence

<400> SEQUENCE: 39
tatataaacc taaccctctc actagcatga aggtaccttg tcgttgaaga gggttaggtt    60
tatata                                                               66

<210> SEQ ID NO 40
<211> LENGTH: 67
<212> TYPE: DNA
<213> ORGANISM: artificial sequence
<220> FEATURE:
<223> OTHER INFORMATION: description of artificial sequence: target
      sequence

<400> SEQUENCE: 40
tatataaacc taaccctctc cactagcatg aaggtacctt gtcgttgaag agggttaggt    60
ttatata                                                              67

<210> SEQ ID NO 41
<211> LENGTH: 68
<212> TYPE: DNA
<213> ORGANISM: artificial sequence
<220> FEATURE:
<223> OTHER INFORMATION: description of artificial sequence: target
      sequence

<400> SEQUENCE: 41
tatataaacc taaccctctc cactagcatg aaggtacctt gtcgttgata gagggttagg    60
tttatata                                                             68

<210> SEQ ID NO 42
<211> LENGTH: 69
<212> TYPE: DNA
<213> ORGANISM: artificial sequence
<220> FEATURE:
<223> OTHER INFORMATION: description of artificial sequence: target
      sequence

<400> SEQUENCE: 42
tatataaacc taaccctcta ccactagcat gaaggtacct tgtcgttgat agagggttag    60
gtttatata                                                            69

<210> SEQ ID NO 43
<211> LENGTH: 70
<212> TYPE: DNA
<213> ORGANISM: artificial sequence
<220> FEATURE:
<223> OTHER INFORMATION: description of artificial sequence: target
      sequence
```

<400> SEQUENCE: 43
tatataaacc taaccctcta ccactagcat gaaggtacct tgtcgttgat tagagggtta    60
ggtttatata                                                          70

<210> SEQ ID NO 44
<211> LENGTH: 71
<212> TYPE: DNA
<213> ORGANISM: artificial sequence
<220> FEATURE:
<223> OTHER INFORMATION: description of artificial sequence: target
      sequence

<400> SEQUENCE: 44
tatataaacc taaccctctg accactagca tgaaggtacc ttgtcgttga ttagagggtt    60
aggtttatat a                                                        71

<210> SEQ ID NO 45
<211> LENGTH: 72
<212> TYPE: DNA
<213> ORGANISM: artificial sequence
<220> FEATURE:
<223> OTHER INFORMATION: description of artificial sequence: target
      sequence

<400> SEQUENCE: 45
tatataaacc taaccctctg accactagca tgaaggtacc ttgtcgttga ttcagagggt    60
taggtttata ta                                                       72

<210> SEQ ID NO 46
<211> LENGTH: 73
<212> TYPE: DNA
<213> ORGANISM: artificial sequence
<220> FEATURE:
<223> OTHER INFORMATION: description of artificial sequence: target
      sequence

<400> SEQUENCE: 46
tatataaacc taaccctctt gaccactagc atgaaggtac cttgtcgttg attcagaggg    60
ttaggtttat ata                                                      73

<210> SEQ ID NO 47
<211> LENGTH: 74
<212> TYPE: DNA
<213> ORGANISM: artificial sequence
<220> FEATURE:
<223> OTHER INFORMATION: description of artificial sequence: target
      sequence

<400> SEQUENCE: 47
tatataaacc taaccctctt gaccactagc atgaaggtac cttgtcgttg attcaagagg    60
gttaggttta tata                                                     74

<210> SEQ ID NO 48
<211> LENGTH: 75
<212> TYPE: DNA
<213> ORGANISM: artificial sequence
<220> FEATURE:
<223> OTHER INFORMATION: description of artificial sequence: target
      sequence

```
<400> SEQUENCE: 48
tatataaacc taaccctctc tgaccactag catgaaggta ccttgtcgtt gattcaagag        60
ggttaggttt atata                                                        75

<210> SEQ ID NO 49
<211> LENGTH: 76
<212> TYPE: DNA
<213> ORGANISM: artificial sequence
<220> FEATURE:
<223> OTHER INFORMATION: description of artificial sequence: target
      sequence

<400> SEQUENCE: 49
tatataaacc taaccctctc tgaccactag catgaaggta ccttgtcgtt gattcagaga        60
gggttaggtt tatata                                                       76

<210> SEQ ID NO 50
<211> LENGTH: 77
<212> TYPE: DNA
<213> ORGANISM: artificial sequence
<220> FEATURE:
<223> OTHER INFORMATION: description of artificial sequence: target
      sequence

<400> SEQUENCE: 50
tatataaacc taaccctctt ctgaccacta gcatgaaggt accttgtcgt tgattcagag        60
agggttaggt ttatata                                                      77

<210> SEQ ID NO 51
<211> LENGTH: 78
<212> TYPE: DNA
<213> ORGANISM: artificial sequence
<220> FEATURE:
<223> OTHER INFORMATION: description of artificial sequence: target
      sequence

<400> SEQUENCE: 51
tatataaacc taaccctctt ctgaccacta gcatgaaggt accttgtcgt tgattcagta        60
gagggttagg tttatata                                                     78

<210> SEQ ID NO 52
<211> LENGTH: 43
<212> TYPE: DNA
<213> ORGANISM: artificial sequence
<220> FEATURE:
<223> OTHER INFORMATION: description of artificial sequence: target
      sequence

<400> SEQUENCE: 52
agagggttag gtttatataa ggtatatata aacctaaccc tct                         43

<210> SEQ ID NO 53
<211> LENGTH: 44
<212> TYPE: DNA
<213> ORGANISM: artificial sequence
<220> FEATURE:
<223> OTHER INFORMATION: description of artificial sequence: target
      sequence

<400> SEQUENCE: 53
agagggttag gtttatataa aggtatatat aaacctaacc ctct                        44
```

```
<210> SEQ ID NO 54
<211> LENGTH: 45
<212> TYPE: DNA
<213> ORGANISM: artificial sequence
<220> FEATURE:
<223> OTHER INFORMATION: description of artificial sequence: target
      sequence

<400> SEQUENCE: 54
agagggttag gtttatataa aggtactata taaacctaac cctct                 45

<210> SEQ ID NO 55
<211> LENGTH: 46
<212> TYPE: DNA
<213> ORGANISM: artificial sequence
<220> FEATURE:
<223> OTHER INFORMATION: description of artificial sequence: target
      sequence

<400> SEQUENCE: 55
agagggttag gtttatatag aaggtactat ataaacctaa ccctct                46

<210> SEQ ID NO 56
<211> LENGTH: 47
<212> TYPE: DNA
<213> ORGANISM: artificial sequence
<220> FEATURE:
<223> OTHER INFORMATION: description of artificial sequence: target
      sequence

<400> SEQUENCE: 56
agagggttag gtttatatag aaggtaccta tataaaccta accctct               47

<210> SEQ ID NO 57
<211> LENGTH: 48
<212> TYPE: DNA
<213> ORGANISM: artificial sequence
<220> FEATURE:
<223> OTHER INFORMATION: description of artificial sequence: target
      sequence

<400> SEQUENCE: 57
agagggttag gtttatatat gaaggtacct atataaacct aaccctct              48

<210> SEQ ID NO 58
<211> LENGTH: 49
<212> TYPE: DNA
<213> ORGANISM: artificial sequence
<220> FEATURE:
<223> OTHER INFORMATION: description of artificial sequence: target
      sequence

<400> SEQUENCE: 58
agagggttag gtttatatat gaaggtacct tatataaacc taaccctct             49

<210> SEQ ID NO 59
<211> LENGTH: 50
<212> TYPE: DNA
<213> ORGANISM: artificial sequence
<220> FEATURE:
<223> OTHER INFORMATION: description of artificial sequence: target
      sequence

<400> SEQUENCE: 59
agagggttag gtttatataa tgaaggtacc ttatataaac ctaaccctct            50
```

```
<210> SEQ ID NO 60
<211> LENGTH: 51
<212> TYPE: DNA
<213> ORGANISM: artificial sequence
<220> FEATURE:
<223> OTHER INFORMATION: description of artificial sequence: target
      sequence

<400> SEQUENCE: 60
agagggttag gtttatataa tgaaggtacc tttatataaa cctaaccctc t            51

<210> SEQ ID NO 61
<211> LENGTH: 52
<212> TYPE: DNA
<213> ORGANISM: artificial sequence
<220> FEATURE:
<223> OTHER INFORMATION: description of artificial sequence: target
      sequence

<400> SEQUENCE: 61
agagggttag gtttatatac atgaaggtac ctttatataa acctaaccct ct           52

<210> SEQ ID NO 62
<211> LENGTH: 53
<212> TYPE: DNA
<213> ORGANISM: artificial sequence
<220> FEATURE:
<223> OTHER INFORMATION: description of artificial sequence: target
      sequence

<400> SEQUENCE: 62
agagggttag gtttatatac atgaaggtac cttgtatata aacctaaccc tct          53

<210> SEQ ID NO 63
<211> LENGTH: 54
<212> TYPE: DNA
<213> ORGANISM: artificial sequence
<220> FEATURE:
<223> OTHER INFORMATION: description of artificial sequence: target
      sequence

<400> SEQUENCE: 63
agagggttag gtttatatag catgaaggta ccttgtatat aaacctaacc ctct         54

<210> SEQ ID NO 64
<211> LENGTH: 55
<212> TYPE: DNA
<213> ORGANISM: artificial sequence
<220> FEATURE:
<223> OTHER INFORMATION: description of artificial sequence: target
      sequence

<400> SEQUENCE: 64
agagggttag gtttatatag catgaaggta ccttgttata taaacctaac cctct        55

<210> SEQ ID NO 65
<211> LENGTH: 56
<212> TYPE: DNA
<213> ORGANISM: artificial sequence
<220> FEATURE:
<223> OTHER INFORMATION: description of artificial sequence: target
      sequence

<400> SEQUENCE: 65
agagggttag gtttatataa gcatgaaggt accttgttat ataaacctaa ccctct       56
```

```
<210> SEQ ID NO 66
<211> LENGTH: 57
<212> TYPE: DNA
<213> ORGANISM: artificial sequence
<220> FEATURE:
<223> OTHER INFORMATION: description of artificial sequence: target
      sequence

<400> SEQUENCE: 66
agagggttag gtttatataa gcatgaaggt accttgtcta tataaaccta accctct          57

<210> SEQ ID NO 67
<211> LENGTH: 58
<212> TYPE: DNA
<213> ORGANISM: artificial sequence
<220> FEATURE:
<223> OTHER INFORMATION: description of artificial sequence: target
      sequence

<400> SEQUENCE: 67
agagggttag gtttatatat agcatgaagg taccttgtct atataaacct aaccctct         58

<210> SEQ ID NO 68
<211> LENGTH: 59
<212> TYPE: DNA
<213> ORGANISM: artificial sequence
<220> FEATURE:
<223> OTHER INFORMATION: description of artificial sequence: target
      sequence

<400> SEQUENCE: 68
agagggttag gtttatatat agcatgaagg taccttgtcg tatataaacc taaccctct        59

<210> SEQ ID NO 69
<211> LENGTH: 60
<212> TYPE: DNA
<213> ORGANISM: artificial sequence
<220> FEATURE:
<223> OTHER INFORMATION: description of artificial sequence: target
      sequence

<400> SEQUENCE: 69
agagggttag gtttatatat agcatgaagg taccttgtcg ttatataaac ctaaccctct       60

<210> SEQ ID NO 70
<211> LENGTH: 61
<212> TYPE: DNA
<213> ORGANISM: artificial sequence
<220> FEATURE:
<223> OTHER INFORMATION: description of artificial sequence: target
      sequence

<400> SEQUENCE: 70
agagggttag gtttatatac tagcatgaag gtaccttgtc gttatataaa cctaaccctc       60
t                                                                      61

<210> SEQ ID NO 71
<211> LENGTH: 62
<212> TYPE: DNA
<213> ORGANISM: artificial sequence
<220> FEATURE:
<223> OTHER INFORMATION: description of artificial sequence: target
      sequence
```

<400> SEQUENCE: 71
agagggttag gtttatatac tagcatgaag gtaccttgtc gtttatataa acctaaccct    60
ct                                                                   62

<210> SEQ ID NO 72
<211> LENGTH: 63
<212> TYPE: DNA
<213> ORGANISM: artificial sequence
<220> FEATURE:
<223> OTHER INFORMATION: description of artificial sequence: target
      sequence

<400> SEQUENCE: 72
agagggttag gtttatataa ctagcatgaa ggtaccttgt cgtttatata aacctaaccc    60
tct                                                                  63

<210> SEQ ID NO 73
<211> LENGTH: 64
<212> TYPE: DNA
<213> ORGANISM: artificial sequence
<220> FEATURE:
<223> OTHER INFORMATION: description of artificial sequence: target
      sequence

<400> SEQUENCE: 73
agagggttag gtttatataa ctagcatgaa ggtaccttgt cgttgtatat aaacctaacc    60
ctct                                                                 64

<210> SEQ ID NO 74
<211> LENGTH: 65
<212> TYPE: DNA
<213> ORGANISM: artificial sequence
<220> FEATURE:
<223> OTHER INFORMATION: description of artificial sequence: target
      sequence

<400> SEQUENCE: 74
agagggttag gtttatatac actagcatga aggtaccttg tcgttgtata taaacctaac    60
cctct                                                                65

<210> SEQ ID NO 75
<211> LENGTH: 66
<212> TYPE: DNA
<213> ORGANISM: artificial sequence
<220> FEATURE:
<223> OTHER INFORMATION: description of artificial sequence: target
      sequence

<400> SEQUENCE: 75
agagggttag gtttatatac actagcatga aggtaccttg tcgttgatat ataaacctaa    60
ccctct                                                               66

<210> SEQ ID NO 76
<211> LENGTH: 67
<212> TYPE: DNA
<213> ORGANISM: artificial sequence
<220> FEATURE:
<223> OTHER INFORMATION: description of artificial sequence: target
      sequence -continued

```
<400> SEQUENCE: 76
agagggttag gtttatatac cactagcatg aaggtacctt gtcgttgata tataaaccta    60
accctct                                                             67

<210> SEQ ID NO 77
<211> LENGTH: 68
<212> TYPE: DNA
<213> ORGANISM: artificial sequence
<220> FEATURE:
<223> OTHER INFORMATION: description of artificial sequence: target
      sequence

<400> SEQUENCE: 77
agagggttag gtttatatac cactagcatg aaggtacctt gtcgttgatt atataaacct    60
aaccctct                                                            68

<210> SEQ ID NO 78
<211> LENGTH: 69
<212> TYPE: DNA
<213> ORGANISM: artificial sequence
<220> FEATURE:
<223> OTHER INFORMATION: description of artificial sequence: target
      sequence

<400> SEQUENCE: 78
agagggttag gtttatataa ccactagcat gaaggtacct tgtcgttgat tatataaacc    60
taaccctct                                                           69

<210> SEQ ID NO 79
<211> LENGTH: 70
<212> TYPE: DNA
<213> ORGANISM: artificial sequence
<220> FEATURE:
<223> OTHER INFORMATION: description of artificial sequence: target
      sequence

<400> SEQUENCE: 79
agagggttag gtttatataa ccactagcat gaaggtacct tgtcgttgat ttatataaac    60
ctaaccctct                                                          70

<210> SEQ ID NO 80
<211> LENGTH: 71
<212> TYPE: DNA
<213> ORGANISM: artificial sequence
<220> FEATURE:
<223> OTHER INFORMATION: description of artificial sequence: target
      sequence

<400> SEQUENCE: 80
agagggttag gtttatatag accactagca tgaaggtacc ttgtcgttga tttatataaa    60
cctaaccctc t                                                        71

<210> SEQ ID NO 81
<211> LENGTH: 72
<212> TYPE: DNA
<213> ORGANISM: artificial sequence
<220> FEATURE:
<223> OTHER INFORMATION: description of artificial sequence: target
      sequence
```

```
<400> SEQUENCE: 81
agagggttag gtttatatag accactagca tgaaggtacc ttgtcgttga ttctatataa      60
acctaaccct ct                                                          72

<210> SEQ ID NO 82
<211> LENGTH: 73
<212> TYPE: DNA
<213> ORGANISM: artificial sequence
<220> FEATURE:
<223> OTHER INFORMATION: description of artificial sequence: target
      sequence

<400> SEQUENCE: 82
agagggttag gtttatatat gaccactagc atgaaggtac cttgtcgttg attctatata      60
aacctaaccc tct                                                         73

<210> SEQ ID NO 83
<211> LENGTH: 46
<212> TYPE: DNA
<213> ORGANISM: artificial sequence
<220> FEATURE:
<223> OTHER INFORMATION: description of artificial sequence: target
      sequence

<400> SEQUENCE: 83
cagcagcagc agcagcaatg aaggtacctc agcagcagca gcagca                     46

<210> SEQ ID NO 84
<211> LENGTH: 49
<212> TYPE: DNA
<213> ORGANISM: artificial sequence
<220> FEATURE:
<223> OTHER INFORMATION: description of artificial sequence: target
      sequence

<400> SEQUENCE: 84
cagcagcagc agcagcatag catgaaggta cccagcagca gcagcagca                  49

<210> SEQ ID NO 85
<211> LENGTH: 52
<212> TYPE: DNA
<213> ORGANISM: artificial sequence
<220> FEATURE:
<223> OTHER INFORMATION: description of artificial sequence: target
      sequence

<400> SEQUENCE: 85
cagcagcagc agcagcaagc atgaaggtac cttgtcagca gcagcagcag ca              52

<210> SEQ ID NO 86
<211> LENGTH: 55
<212> TYPE: DNA
<213> ORGANISM: artificial sequence
<220> FEATURE:
<223> OTHER INFORMATION: description of artificial sequence: target
      sequence

<400> SEQUENCE: 86
cagcagcagc agcagcatag catgaaggta ccttgtcgca gcagcagcag cagca           55

<210> SEQ ID NO 87
<211> LENGTH: 58
<212> TYPE: DNA
<213> ORGANISM: artificial sequence
```

```
<220> FEATURE:
<223> OTHER INFORMATION: description of artificial sequence: target
      sequence

<400> SEQUENCE: 87
cagcagcagc agcagcacta gcatgaaggt accttgtcgt tcagcagcag cagcagca        58

<210> SEQ ID NO 88
<211> LENGTH: 61
<212> TYPE: DNA
<213> ORGANISM: artificial sequence
<220> FEATURE:
<223> OTHER INFORMATION: description of artificial sequence: target
      sequence

<400> SEQUENCE: 88
cagcagcagc agcagcacac tagcatgaag gtaccttgtc gttgcagcag cagcagcagc        60
a                                                                       61

<210> SEQ ID NO 89
<211> LENGTH: 64
<212> TYPE: DNA
<213> ORGANISM: artificial sequence
<220> FEATURE:
<223> OTHER INFORMATION: description of artificial sequence: target
      sequence

<400> SEQUENCE: 89
cagcagcagc agcagcacca ctagcatgaa ggtaccttgt cgttgatcag cagcagcagc        60
agca                                                                    64

<210> SEQ ID NO 90
<211> LENGTH: 59
<212> TYPE: DNA
<213> ORGANISM: artificial sequence
<220> FEATURE:
<223> OTHER INFORMATION: description of artificial sequence: target
      sequence

<400> SEQUENCE: 90
cagcagcagc agcagcagca gcagcagcag cagcagcagc agcagcagca gcagcagca        59

<210> SEQ ID NO 91
<211> LENGTH: 375
<212> TYPE: PRT
<213> ORGANISM: artificial sequence
<220> FEATURE:
<223> OTHER INFORMATION: Restriction endonuclease FokI, catalytic domain

<400> SEQUENCE: 91

Met Ala Ser Gly Pro Asn Arg Gly Val Thr Lys Gln Leu Val Lys Ser
1               5                   10                  15

Glu Leu Glu Glu Lys Lys Ser Glu Leu Arg His Lys Leu Lys Tyr Val
            20                  25                  30

Pro His Glu Tyr Ile Glu Leu Ile Glu Ile Ala Arg Asn Ser Thr Gln
        35                  40                  45

Asp Arg Ile Leu Glu Met Lys Val Met Glu Phe Phe Met Lys Val Tyr
    50                  55                  60

Gly Tyr Arg Gly Lys His Leu Gly Gly Ser Arg Lys Pro Asp Gly Ala
65                  70                  75                  80

Ile Tyr Thr Val Gly Ser Pro Ile Asp Tyr Gly Val Ile Val Asp Thr
                85                  90                  95
```

-continued

```
Lys Ala Tyr Ser Gly Gly Tyr Asn Leu Pro Ile Gly Gln Ala Asp Glu
            100             105             110

Met Gln Arg Tyr Val Glu Glu Asn Gln Thr Arg Asn Lys His Ile Asn
            115             120             125

Pro Asn Glu Trp Trp Lys Val Tyr Pro Ser Ser Val Thr Glu Phe Lys
130             135             140

Phe Leu Phe Val Ser Gly His Phe Lys Gly Asn Tyr Lys Ala Gln Leu
145             150             155             160

Thr Arg Leu Asn His Ile Thr Asn Cys Asn Gly Ala Val Leu Ser Val
            165             170             175

Glu Glu Leu Leu Ile Gly Gly Glu Met Ile Lys Ala Gly Thr Leu Thr
            180             185             190

Leu Glu Glu Val Arg Arg Lys Phe Asn Asn Gly Glu Ile Asn Phe Gly
            195             200             205

Ser Ser Gly Val Asp Leu Arg Thr Leu Gly Tyr Ser Gln Gln Gln
            210             215             220

Glu Lys Ile Lys Pro Lys Val Arg Ser Thr Val Ala Gln His His Glu
225             230             235             240

Ala Leu Val Gly His Gly Phe Thr His Ala His Ile Val Ala Leu Ser
            245             250             255

Gln His Pro Ala Ala Leu Gly Thr Val Ala Val Lys Tyr Gln Asp Met
            260             265             270

Ile Ala Ala Leu Pro Glu Ala Thr His Glu Ala Ile Val Gly Val Gly
            275             280             285

Lys Gln Trp Ser Gly Ala Arg Ala Leu Glu Ala Leu Leu Thr Val Ala
            290             295             300

Gly Glu Leu Arg Gly Pro Pro Leu Gln Leu Asp Thr Gly Gln Leu Leu
305             310             315             320

Lys Ile Ala Lys Arg Gly Gly Val Thr Ala Val Glu Ala Val His Ala
            325             330             335

Trp Arg Asn Ala Leu Thr Gly Ala Pro Leu Asn Leu Thr Gly Asp Ala
            340             345             350

Arg Gly Ile Arg Ser Arg Ala Ser Arg Ser Ile Val Ala Gln Leu Ser
            355             360             365

Arg Pro Asp Pro Ser Ala Asp
370             375
```